(12) United States Patent
Mochitate

(10) Patent No.: US 8,765,473 B2
(45) Date of Patent: Jul. 1, 2014

(54) METHOD OF PREPARING BASEMENT MEMBRANE, METHOD OF CONSTRUCTING BASEMENT MEMBRANE SPECIMEN, RECONSTITUTED ARTIFICIAL TISSUE USING THE BASEMENT MEMBRANE SPECIMEN AND PROCESS FOR PRODUCING THE SAME

(75) Inventor: Katsumi Mochitate, Tsukuba (JP)

(73) Assignees: Japan Science and Technology Agency, Saitama (JP); National Institute for Environmental Studies, Ibaraki (JP)

( * ) Notice: Subject to any disclaimer, the term of this patent is extended or adjusted under 35 U.S.C. 154(b) by 1656 days.

(21) Appl. No.: 11/599,953

(22) Filed: Nov. 15, 2006

(65) Prior Publication Data

US 2007/0122796 A1 May 31, 2007

Related U.S. Application Data

(60) Division of application No. 10/809,218, filed on Mar. 25, 2004, now Pat. No. 7,399,634, which is a continuation-in-part of application No. PCT/JP02/09841, filed on Sep. 25, 2002.

(30) Foreign Application Priority Data

| Sep. 25, 2001 | (JP) | 2001-292510 |
| Sep. 25, 2001 | (JP) | 2001-292675 |
| Sep. 25, 2001 | (JP) | 2001-292676 |
| Sep. 25, 2001 | (JP) | 2001-292677 |
| Sep. 24, 2002 | (JP) | 2002-278243 |
| Sep. 24, 2002 | (JP) | 2002-278244 |

(51) Int. Cl.
| C12N 5/00 | (2006.01) |
| C12N 5/02 | (2006.01) |
| C12N 5/07 | (2010.01) |
| C12N 5/10 | (2006.01) |

(52) U.S. Cl.
USPC ............ 435/397; 435/325; 435/357; 435/395

(58) Field of Classification Search
None
See application file for complete search history.

(56) References Cited

U.S. PATENT DOCUMENTS 5,326,357 A * 7/1994 Kandel ...................... 623/23.72

OTHER PUBLICATIONS

Enrico Cagliero, et al., Increased Expression of Basement Membrane Components in Human Endothelial Cells Cultured in High Glucose, J. of Clinical Investigation (1988) vol. 82, p. 735-738.

Margo P. Cohen, et al., Glycated Albumin Modified by Amadori Adducts Modulates Aortic Endothelial Cell Biology, Molecular and Cellular Biochemistry (1995) vol. 143, p. 73-79.

Joseph El Khoury, et al, Macrophages Adhere to Gluose-Modified Basement Membrane Collagen IV via Their Scavenger Receptors, The Journal of Biological Chemistry, (1994) vol. 269, No. 14, p. 10197-10200.

Herve Emonard, et al., Interactions Between Fibroblasts and a Reconstituted Basement Membrane Matrix, The Journal of Investigative Dermatology (1987) vol. 89, No. 2, p. 156-163.

Debabrata Ghosh, et al., Functional Differentiation of Mouse Uterine Epithelial Cells Grown on Collagen Gels or Reconstituted Basement Membranes, In Vitro Cell. Dev. Biol. (1991) vol. 27A.

K. Jansson, et al., Time-Course for In Vitro Development of Basement Membrane, Gap Junctions, and Repair by Adult Endothelial Cells Seeded on Precoated ePTFE, Eur. J. Vac. Endovasc. Surg. (1998) vol. 16, p. 334-341.

A. Stevenson, et al., Biochemical Markers of Basement Membrane Disturbances and Occupational Exposure to Hydrocarbons and Mixed Solvents, QJ Med. (1995) vol. 88, p. 23-28.

A Furuyama et al., "Assembly of the exogenous extracellular matrix during basement membrane formation by alveolar epithelial cells in vitro", Journal of Cell Science, vol. 113, pp. 859-868, 2000.

* cited by examiner

*Primary Examiner* — Debbie K Ware
(74) *Attorney, Agent, or Firm* — Frommer Lawrence & Haug LLP

(57) ABSTRACT

A basement membrane having a barrier function is formed by culturing alveolar epithelial cells or vascular endothelial cells on a fibrous collagen matrix coated with a polymer having a sugar chain that can localize a receptor that has an activity to accumulate a basement membrane component on the basal surface of the cells having an ability to form a basement membrane. A reconstructed artificial tissue is obtained by seeding and culturing desired homogeneous or heterogeneous cells on the basement membrane specimen constructed by the following process: (i) the cells having an ability to form a basement membrane adhered onto a support structure through a basement membrane are treated with a surface active agent; (ii) the lipid component of cells is lysed; (iii) the mixture of an alkaline solution and a protease inhibitor is used to lyse the protein remained on the surface of the basement membrane of the cells.

10 Claims, 16 Drawing Sheets

METHOD OF PREPARING BASEMENT MEMBRANE, METHOD OF CONSTRUCTING BASEMENT MEMBRANE SPECIMEN, RECONSTITUTED ARTIFICIAL TISSUE USING THE BASEMENT MEMBRANE SPECIMEN AND PROCESS FOR PRODUCING THE SAME

REFERENCE TO RELATED APPLICATIONS

This application is a divisional of U.S. Application No. 10,809,218 filed on Mar. 25, 2004 now U.S. Pat. No. 7,399,634, which is a continuation-in-part of International Patent Application PCT/JP02/09841 filed Sep. 25, 2002 and published as WO 03/026712 on Apr. 3, 2003, which claims priority to Japanese Patent Application Numbers 2001-292510, 2001-292675, 2001-292676, 2001-292677 and 2001-292510, all of which were filed Sep. 25, 2001, and to Japanese Patent Application Numbers 2002-278243 and 2002-278244, which were both filed on Sep. 24, 2002. Each of the above applications, and each document cited in this text and in each of the above applications ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended.

TECHNICAL FIELD

The present invention relates to: a method for preparing a basement membrane which is extracellular matrices having a function to control morphology, differentiation, proliferation, motility, function expression and the like of cells; a tissue model which can be obtained by the above-mentioned method for preparing a basement membrane; a test tissue kit including said tissue model (hereinafter referred to as "the present invention 1"). The present invention also relates to a method for constructing a basement membrane specimen, and a basement membrane specimen which can be obtained by said construction method (hereinafter referred to as "the present invention 2"). The present invention further relates to a reconstituted artificial tissue (reconstituted tissue model) of human and the like wherein a basement membrane specimen is used, for example, a reconstituted artificial tissue (reconstituted tissue model) such as an artificial blood vessel, an artificial lung, an artificial liver, an artificial kidney, an artificial skin, an artificial cornea and the like, and a process for producing the same (hereinafter referred to as "the present invention 3"). The present invention still further relates to: a basement membrane specimen and an artificial tissue formed on a protein support structure which is temporarily adhered to plastic surface, more particularly to a basement membrane specimen which is formed on a protein support attached to plastic surface but is temporarily adhered to the same in order to be physically detached from plastic surface when desired; an artificial tissue (tissue model) such as an artificial blood vessel, an artificial lung, an artificial liver, an artificial kidney, an artificial skin, an artificial cornea and the like; a process for producing the same (hereinafter referred to as "the present invention 4").

BACKGROUND ART

An epithelial tissue, which is a cell layer covering the inside and outside surface of an animal body, such as an epidermis, a corneal epithelium, an alveolar epithelium, a mucosal epithelium of digestive system, renal glomerular epithelium, hepatic parenchymal cells and the like, prevents the invasion of an exogenous material (microorganism, allergen, chemical substance, etc.) from the external world. The outer interface epithelial cells that constitutes said epithelial tissue is called apical, and the inside undersurface is called basal. Just beneath said basal surface, there is a thin film structure of 50-100 nm thickness called a basement membrane comprised of extracellular matrices (ECM) such as proteins, proteoglycans and the like (not including cells). Abasement membrane is considered to be an essential structure for immature epithelial cells to proliferate, to differentiate into mature cells, and to express its original morphology or function. In other words, without a basement membrane, an epithelial tissue cannot maintain itself or achieve its original performance. Although an epithelial cell layer of multi-layer or monolayer prevents the invasion of an exogenous material from the external world as a barrier, a basement membrane itself also acts as a physical barrier. Thus, epithelial cells comprising an epithelial tissue collaborate with a basement membrane to form a solid barrier and to protect the internal vital activity.

A basement membrane, which is a specific membranous structure of extracellular matrices formed on the interface of parenchymal cells, such as epithelial cells, endothelial cells, muscle cells, adipocytes, Schwann cells and the like, and connective tissue, is universally found in respective tissue/organ of a living body, however, some basement membranes (?) are highly specialized such as a renal glomerular capillary loop, a nervous synapse membrane and the like. Therefore, not only its function to adhere cells to an interstitium, but also its function to selectively permeate a substance/cells, and to induce the differentiation of cells are also disclosed. In renal glomerulus, negative electric charge of a basement membrane is considered to be responsible for the filtration function of kidney, and said negative electric charge is traditionally known to be charged by heparan sulfate proteoglycan (HSPG) which is currently called perlecan. HSPG is widely distributed not only to a renal glomerular basement membrane but also to various basement membranes as its basic component in the same manner as type IV collagen, laminin, entactin and the like.

An extracellular matrix, especially abasement membrane, is now gradually known to be deeply involved not only in physiological phenomena such as generation or differentiation of an individual as mentioned above, but also in formation of pathology such as proliferative metastasis of cancer, inflammation and the like. Therefore, clarification of the function of its constituent protein has been an important task. For example, laminin, which is a main glycoprotein of a basement membrane, is a complex comprised of three subunits α, β, and γ, fifteen types of its isoforms are known, and they are expressed tissue-specifically and at each step of development. Laminin is a complicated macromolecule of 900,000 molecular weight having various bioactivities, and over 20 types of laminin receptors are reported.

The interaction between a component of a basement membrane, which is a thin extracellular matrix layer wherein cells can be adhered, and epithelial cells influences the cell function such as migration, proliferation, differentiation and the like (Crouch et al., Basement membrane. In The Lung (ed. R. G. Crystal and J. B. West), pp 53.1-53.23. Philadelphia Lippincott-Raven. 1996). As for the main components of a basement membrane, laminin, type IV collagen, heparan sulfate proteoglycan (HSPG), and entactin are known as mentioned above (Curr. Opin. Cell Biol. 6, 674-681, 1994), and mesenchymal cells are considered to play an important role for the synthesis of a basement membrane component including isoform of laminin and type IV collagen (Matrix Biol. 14, 209-211, 1994; J. Biol. Chem. 268, 26033-26036, 1993), however, the role of epithelial cells is also important. HSPG is believed to have been derived from epithelial cells, however, laminin, type IV collagen, and entactin are synthesized in vivo by both of epithelial cells and mesenchymal cells (Development 120, 2003-2014, 1994; Gastroenterology 102, 1835-1845, 1992). Many attempts have been made to construct an epithelial tissue model in vitro showing a continuous lamina densa. Tissue models of intestine (J. Cell Biol. 133, 417-430, 1996) and skin (J. Invest. Dermatol. 105, 597-601, 1995; J. Invest. Dermatol. 109, 527-533, 1997; Dev. Dynam. 197. 255-267, 1993) and the like have been studied, and some of basement membrane components derived from mesenchymal cells have been found to play an important role in the formation of a basement membrane.

Several methods to constitute a basement membrane by culturing epithelial cells, and to constitute epithelial cells wherein a basement membrane structure is present just beneath the basal surface have been reported. For example, the present inventors have reported that a basement membrane can be formed in vitro by coculturing alveolar epithelial cells and pulmonary fibroblasts (Cell Struc. Func., 22:603-614, 1997). It has been reported that: if pulmonary fibroblasts, being embedded in type I collagen gel, were cultured, the collagen gel was contracted and became more solid by pulmonary fibroblasts, and extracellular matrices being secreted and adsorbed to collagen fiber around the cells and deposited; such contracted collagen gel by fibroblasts is called a pseudo-interstitium since it is similar to an interstitium in vivo; and if type II alveolar epithelial cell lines (SV40-T2) were cultured on such a pseudointerstitial tissue for approximately 14 days (T2-Fgel), basement membrane components such as type IV collagen, laminin and the like in extracellular matrices secreted by pulmonary fibroblasts were diffused in a culture medium and reached to the basal surf ace of the above-mentioned type II alveolar epithelial cell lines, and used as a material for the constitution of a basement membrane, and as a result, a basement membrane structure was formed.

It is also reported that dilute neutral collagen solution was incubated at 37° C. in 5% $CO_2$, and collagen fiber was formed, the air-dried collagen fibrous matrix (fib) which was air-dried in aseptic condition was used as an alternative for the above-mentioned pseudointerstitium in a same manner as the above-mentioned coculture of alveolar epithelial cells and pulmonary fibroblasts to form a basement membrane (Eur. J. Cell Biol., 78:867-875, 1999; J. Cell Sci., 113:859-868, 2000). In this process, if the concentration of collagen solution is high, there will be less or no gap in fibrous collagen matrix formed, and if epithelial cells are cultured for a long term (10 days-2 weeks) for the purpose of forming a basement membrane, cells are detached and floated (e.g. Becton Dickinson, Fibrous collagen coat culture insert), therefore, the concentration of collagen solution is considered to be optimum at 0.3-0.5 mg/ml (Eur. J. Cell. Biol., 78:867-875, 1999; J. Cell Sci., 113:859-868, 2000).

Type II alveolar epithelial cell lines (SV40-T2) were cultured on fibrous collagen matrix wherein Matrigel (the registered trademark of Becton Dickinson) was added, instead of using collagen matrix wherein fibrous cells were embedded. In this case, Matrigel functioned as an exogenous resource of basement membrane components. Matrigel is a mixture of basement membrane components extracted from Engelbreth-Holm-Swarm tumor matrix (J. Exp. Med. 145, 204-220, 1977), and contains laminin-1, entactin, type IV collagen, and perlecan, as well as various cytokines that possibly influence the ECM synthesis (Exp. Cell Res. 202, 1-8, 1992). In order to trace the Matrigel components incorporated in a basement membrane, Matrigel was labeled with biotin, and the process where in the formation of a basement membrane was accelerated depending on the amount of Matrigel, and a basement membrane matrix being secreted in punctiform manner deposited in a sheet form, then a basement membrane development was observed by immunofluorescent staining of basement membrane components such as laminin, entactin, type IV collagen, perlecan, and the electron micrographic monitoring. As a result, it has been found that stable exogenous laminin-1 and entactin are largely involved in the complete development of a basement membrane by the above-mentioned epithelial cells in vitro at the lower surface of alveolar epithelial cells (J. Cell Sci., 113:859-868, 2000).

Further, an artificial skin formation promoting agent and skin basement membrane stabilizing agent comprising matrix metalloproteinase inhibitor or matrix metalloproteinase inhibitor and matrix protein production promoting agent; as well as a production method of artificial skin comprising adding matrix metalloproteinase inhibitor or matrix metalloproteinase inhibitor and matrix protein production promoting agent to an artificial skin formation medium are known (Japanese Laid-Open Patent Application No. 2001-269398).

The present inventors made a study on a process to form a basement membrane structure just beneath the basal surface of epithelial cells on a fibrous collagen matrix by the coculture with fibroblasts-embedded collagen gel, and by the culture in the presence of TGF-β or Matrigel. In the case of type II alveolar epithelial cells, it was confirmed that a basement membrane was formed in the following cases as shown in FIG. 1: the case wherein type II alveolar epithelial cells were cultured on pulmonary fibroblast-embedded collagen matrix in upper wells of culture inserts (collagen gel wherein fibrous cells are embedded) (T2-Fgel); the case wherein they were cultured on fibrous collagen substratum on upper wells in coculture with alveolar fibroblasts-embedded collagen matrix in lower wells (T2-fib-Fcm); the case wherein they were cultured on fibrous collagen substratum in upper wells in the presence of Matrigel coat on lower wells (T2-fib-MG); the case wherein they are cultured on fibrous collagen substratum in upper wells in the presence of growth factor TGF-β in upper and lower wells (T2-fib-TGFβ). However, it was also confirmed that type II alveolar epithelial cells were unable to constitute a basement membrane without the supply of, for example, a fibroblast, exogenous basement membrane components from Matrigel or a growth factor TGF-β, since the endogenous basement membrane components from type II alveolar epithelial cells are not enough for the cells to assemble a basement membrane structure effectively. However, following problems still remained: a problem of frequent troubles that, when fibroblasts secreting basement membrane components and a growth factor of TGF-β are used, gel contraction occurs during the culture, and the fibroblasts are peeled off from plastic membrane together with alveolar epithelial cells; a problem that reagents used to peel alveolar epithelial cells for the separation of basemen membrane specimen tend to remain inside the gel if fibroblasts are embedded, and the wash procedure of such reagents is complicated; a problem that if some parts of cells remain, it may become an antigen, a problem that culture protocol for the formation of a basement membrane its-elf is complicated. Further, there has been also a problem that if fibroblasts alternative such as Matrigel and the like or a growth factor TGF-β is used as a resource of basement membrane component, said Matrigel and said growth factor TGF-β are expensive, and it is not advantageous in terms of the cost.

On the other hand, constitution of a basement membrane by endothelial cells (EC) was also considered. Although a basement membrane which is present just beneath the basal surface of endothelial cells also contributes to the expression and the maintenance of functions in endothelial cells, and a basement membrane of endothelial cells plays a role of a barrier when inflammatory cells invade into tissue from blood vessel, or when cancer cells metastasize, a basement membrane of vascular endothelial cells cannot be easily formed as for the case of epithelial cells. In the formation of a basement membrane by vascular endothelial cells, unlike the case of type II alveolar epithelial cells, as shown in FIG. 2, a basement membrane was not formed in the following cases with the exception of the case of (EC-Fgel) wherein the culture was carried out on fibroblast-embedded collagen matrix in upper wells; the case wherein the culture was carried out on fibrous collagen substratum in(on) upper wells in the presence of pulmonary fibroblasts-embedded collagen matrix in lower wells (EC-fib-Fcm); the case wherein the culture was carried out on fibrous collagen substratum in upper wells in the presence of Matrigel coat in lower wells (EC-fib-MG); the case wherein the culture was carried out on fibrous collagen matrix in upper wells (EC-fib).

In the meantime, the present inventors have reported that epithelial cells can be automatically detached from a basement membrane if alveolar epithelial cells which formed the above-mentioned basement membrane are treated with 0.18 M of hydrogen peroxide solution for 10 minutes, continued to culture for an additional day (Cell Struc. Func., 22, 603-614, 1997). In such process, however, it has been found to be a problem that there are cases that artificial human tissue having sufficient physiological activity such as function expression and maintenance of cells even if homogeneous or heterogeneous cells having a certain ability to form a basement membrane are seeded and cultured on said basement membrane since there are some cases wherein the detachment of cells from a basement membrane is insufficient, and a part of a basement membrane is damaged.

The object of the present invention 1 is to provide: a method for preparing a basement membrane which is extracellular matrices having a function to control morphology, differentiation, proliferation, motility, function expression and the like of cells, particularly a method for preparing a basement membrane with which cells having an ability to form a basement membrane such as epithelial cells, endothelial cells and the like can effectively activate an endogenous basement membrane component; a tissue model which can be obtained by the above-mentioned method for preparing a basement membrane; a test tissue kit including said tissue model. The object of the present invention 2 is to easily and in the short term provide a basement membrane specimen having a function to control morphology, differentiation, proliferation, motility, function expression and the like of cells when a certain homogeneous or heterogeneous cells laving an ability to form a basement membrane are seeded and cultured. The object of the present invention 3 is to provide a process for producing a reconstituted artificial tissue having versatility wherein desired artificial tissue can be produced easily and efficiently in the short term at any time and any place when needed by seeding and culturing certain cells which are homogeneous or heterogeneous to cells which formed a basement membrane using a basement membrane specimen having a function to control morphology, differentiation, proliferation, motility, function expression and the like of cells as a common base material for tissue construction. Another object of the present invention 3 is to provide a reconstituted artificial tissue such as a tissue model, an organ model and the like, which can be obtained by said process for producing an artificial tissue, which has cell layers and a basement membrane structure with barrier function original to a living body, and which can be advantageously applied to pharmacological test, toxicity test or the like of chemical substances. The object of the resent invention 4 is to provide a basement membrane specimen which is extracellular matrices having a function to control morphology, differentiation, proliferation, motility, function expression and the like of cells, with much higher versatility since it is possible to transplant while maintaining the structure of a basement membrane, and which is formed on a protein support structure which is temporarily adhered to plastic surface in order to be physically detached from plastic surface when needed while it is adsorbed and fixed on plastic surface when a basement membrane and an artificial tissue are prepared. The examples include: a basement membrane specimen formed on a collagen fiber; an artificial tissue and an artificial organ such as an artificial blood vessel, an artificial lung, an artificial liver, an artificial kidney, an artificial skin, an artificial cornea and the like; for example, an artificial tissue on a collagen fiber which formed a basement membrane structure on a matrix just beneath the cells.

Basement membrane components secreted from the cells having an ability to be assembled into a basement membrane by such as epithelial cells, endothelial cells and the like, or from fibroblasts, cannot automatically form a basement membrane structure by themselves, and needs a receptor which is considered to be localized on the surface of the cells having an ability to form a basement membrane such as epithelial cells, endothelial cells and the like, or particularly on the basal surface of said cells. The identity of said receptor, however, is not clearly known at the moment including the concern whether it is a single protein. The present inventors, in the course of a keen study on the mechanism of a basement membrane formation, obtained the knowledge that type II alveolar epithelial cells or vascular endothelial cells express receptors for sugar chains on their basal surface since type II alveolar epithelial cells or vascular endothelial cells can be adhered to a polymer having a certain sugar chain in vitro, namely a sugar chain which can localize a receptor having an activity to accumulate a basement membrane component on the basal surface of the cells having an ability to form a basement membrane, e.g. a sugar-chain coat having β-D-glucopyranosyl nonreducing end or 2-acetoamide-2-deoxy- β-D-glucopyranosyl nonreducing end. Secondly, as a result of culturing type II alveolar epithelial cells or vascular endothelial cells on fibrous collagen substratum coated with the above-mentioned polymer, the present inventors have found that a basement membrane having a barrier function similar to the one seen in in vivo is armed just beneath the type II alveolar epithelial cells or vascular endothelial cells. It was also found that although the supply of a basement membrane component such as a Matrigel and the like, and the addition of TGF-β was not necessary for the formation of said basement membrane, if Matrigel was added, construction of a basement membrane was significantly accelerated, the culture term was long enough with a week, and the basement membrane became several fold thick. The knowledge that the above-mentioned fact is a result of that the receptor against the above-mentioned sugar chain was involved to progress the basement membrane formation was obtained. The present invention 1 has been completed based on such knowledge.

DISCLOSURE OF THE INVENTION

The present invention relates to: a method for preparing a basement membrane wherein cells having an ability to form a basement membrane are cultured on a support structure with a sugar-chain coat which can localize a receptor having an activity to accumulate basement membrane components onto a basal surface of the cells having an ability to form a basement membrane (paragraph 1); the method for preparing a basement membrane according to paragraph 1, herein the cells having an ability to form a basement membrane are cultured on of a support structure with both opposite surfaces coated by a sugar chain (paragraph 2); the method for preparing a basement membrane according to paragraph 1 or 2, wherein a component secreted from the cells having an ability to form a basement membrane is used as a basement membrane component (paragraph 3); the method for preparing a basement membrane according to any of paragraphs 1-3, where in a sugar-chain coat, which can possibly adhere the cells having an ability to form a basement membrane onto a support structure through the binding between a sugar chain or a part of a sugar chain and a receptor, is used (paragraph 4); the method for preparing a basement membrane according to paragraph 4, wherein a sugar-chain coat is used, the sugar chain or a part of the sugar chain that binds to a receptor can be replaced by a basement membrane component (paragraph 5); the method for preparing a basement membrane according to any of paragraphs 1-5, wherein the support structure with a sugar-chain coat is a support structure coated with a polymer having a sugar chain (paragraph 6); the method for preparing a basement membrane according to paragraph 6, wherein the polymer having a sugar chain is a polymer having a sugar chain with β-D-glucopyranosyl nonreducing end or 2-acetoamide-2-deoxy-β-D-glucopyranosyl nonreducing end (paragraph 7); the method for preparing a basement membrane according to paragraph 7, wherein one or more types of polymers selected from PV-GlcNAc, PV-CA and PV-Lam is used as the polymer having a sugar chain (paragraph 8).

The present invention is also related to: the method for preparing a basement membrane according to any of paragraphs 1-8, wherein the cells having an ability to form a basement membrane are cocultured with fibroblasts or their alternatives (paragraph 9); the method for preparing a basement membrane according to any of paragraphs 1-9, wherein the cells having an ability to form a basement membrane are cultured in the presence of one or more types of basement membrane components (paragraph 10); the method for preparing a basement membrane according to any of paragraphs 1-10, wherein the cells having an ability to form a basement membrane are cultured in the presence of TGF-β (transforming growth factor) (paragraph 11); the method for preparing a basement membrane according to any of paragraphs 1-11, wherein the cells having an ability to form a basement membrane are epithelial cells, endothelial cells or mesenchymal cells (paragraph 12); the method for preparing a basement membrane according to any of paragraphs 1-12, wherein the cells and/or fibroblasts having an ability to form a basement membrane are basement membrane component-hyperexpressing cells into which genes of one or more types of a basement membrane component are transfected (paragraph 13); the method for preparing a basement membrane according to any of paragraphs 1-13, wherein the support structure is a fibrous collagen (paragraph 14); a tissue model which can be obtained by the method for preparing a basement membrane according to any of paragraphs 1-14 (paragraph 15); a test tissue kit including a tissue model which can be obtained by the method for preparing a basement membrane according to any of paragraphs 1-14 (paragraph 16).

The present inventors found the following facts: if an surface active agent e.g. 0.1% Triton X-100 (Calbiochem-Novabiochem Corporation) is used for the cells wherein the basement membrane obtained by the above-mentioned present invention 1 is formed, lipid component of the cells is lysed by its surface activity; if an alkaline solution e.g. 10-50 mM of $NH_3$ is used, protein residues remained on the basement membrane of cells is lysed; if protease inhibitors cocktail (PIC) is used, degradation of a basement membrane by endogenous proteases and the like in lysosomes being liberated when cells are lysed is suppressed; if desired homogeneous or heterogeneous cells having an ability to form a basement membrane are seeded and cultured, a basement membrane specimen having a function to control morphology, differentiation, proliferation, motility, function expression and the like of cells can be obtained in the short term. Thus, the present invention 2 has been completed.

The present invention 2 relates to: a method for constructing a basement membrane specimen wherein cells having an ability to form a basement membrane adhered onto a support structure through a basement membrane are removed using a solvent having the ability to lyse lipid of the cells and an alkaline solution (paragraph 17); the method for constructing a basement membrane specimen according to paragraph 17, wherein the treatment to remove proteinous and nucleic residues using an alkaline solution is conducted after or at the same time as the delipidating treatment using a solvent having the ability to lyse lipid is conducted (paragraph 18); the method for constructing a basement membrane specimen according b paragraph 17 or 18, wherein the solvent having the ability to lyse lipid is a surface active agent (paragraph 19); the method for constructing a basement membrane specimen according to paragraph 19, wherein the surface active agent is Triton X-100 (paragraph 20); the method for constructing a basement membrane specimen according to any of paragraphs 17-20, wherein the alkaline solution is an alkaline solution with pH 8-14 (paragraph 21); the method for constructing a basement membrane specimen according to paragraph 21, wherein the alkaline solution is an alkaline solution with pH 9-10 (paragraph 22); the method for constructing a basement membrane specimen according to any of paragraphs 17-22, wherein a protease inhibitor is further used (paragraph 23).

The present invention-2 also relates to: the method for constructing a basement membrane specimen according to any of paragraphs 17-23, wherein the basement membrane is a basement membrane prepared by culturing the cells having an ability to form a basement membrane on a collagen gel wherein fibroblasts are embedded (paragraph 24); the method for constructing a basement membrane specimen according to any of paragraphs 17-24, wherein the basement membrane is a basement membrane prepared by culturing the cells having an ability to form a basement membrane on a support structure with a sugar-chain coat which can localize a receptor having an activity to accumulate a basement membrane component on the basal surface of the cells having an ability to form a basement membrane (paragraph 25); the method for constructing a basement membrane specimen according to any of paragraphs 17-25, wherein the basement membrane is a basement membrane prepared by culturing the cells having an ability to form a basement membrane in the presence of a matrix metalloproteinase (paragraph 26); the method for constructing a basement membrane specimen according to any of paragraphs 17-26, wherein the basement membrane is a basement membrane prepared by culturing a basement membrane component and/or growth factor hyperexpressing cells into which one or more types of genes and/or growth factors of a basement membrane component are introduced (paragraph 27); a basement membrane specimen which can be obtained by the method for constructing a basement membrane specimen according to any of paragraphs 17-27 (paragraph 28); the basement membrane specimen according to paragraph 28, which is detached from a support structure (paragraph 29).

The present inventors also have found that as a result of seeding and culturing desired homogeneous or heterogeneous cells having an ability to form a basement membrane on the basement membrane specimen which can be obtained by the above-mentioned present invention 2, an artificial tissue having a barrier function original to a living body can be constituted.

Thus, the present invention 3 relates to: a process for producing a reconstituted artificial tissue wherein certain cells having an ability to form a basement membrane are seeded and cultured on a basement membrane specimen or amorphously basement membrane components-deposited specimen (paragraph 30); the process for producing a reconstituted artificial tissue according to paragraph 30, wherein the cells having an ability to form a basement membrane have a different origin from that of a basement membrane specimen or amorphously basement membrane components-deposited specimen (paragraph 31); the process for producing a reconstituted artificial tissue according to paragraph 30 or 31, wherein the basement membrane specimen or the amorphously basement membrane components-deposited specimen is obtained by removing the cells having an ability to form a basement membrane which are adhered onto a support structure through a basement membrane or basement membrane components-amorphous deposits using a solvent having the ability to lyse lipid of the cells and an alkaline solution (paragraph 32); the process for producing a reconstituted artificial tissue according to paragraph 32, wherein the solvent having the ability to lyse lipid of cells is a surface active agent (paragraph 33); the process for producing a reconstituted artificial tissue according to paragraph 32 or 33, wherein the alkaline solution is an alkaline solution with pH 8-14 (paragraph 34); the process for producing a reconstituted artificial tissue according to paragraph 34, wherein the alkaline solution is an alkaline solution with pH 9-10 (paragraph 35); the process for producing a reconstituted artificial tissue according to any of paragraphs 32-35, wherein a protease inhibitor is further used (paragraph 36); the process for producing a reconstituted artificial tissue according to any of paragraphs 30-36, wherein the basement membrane specimen or the basement membrane components-amorphous deposits specimen is obtained from a basement membrane or a basement membrane components-amorphous deposits prepared by culturing the cells having an ability to form a basement membrane on a collagen gel wherein fibroblasts are embedded (paragraph 37); the process for producing a reconstituted artificial tissue according to any of paragraphs 30-37, wherein the basement membrane specimen or the basement membrane components-amorphous deposits specimen is obtained from a basement membrane or a basement membrane components-amorphous deposits prepared by culturing the cells having an ability to form a basement membrane on a support structure with a sugar chain-coat which can localize a receptor having an activity to accumulate a basement membrane component onto the basal surface of the cells having an ability to form a basement membrane or the surface of the basement membrane components-amorphous deposits (paragraph 38); the process for producing a reconstituted artificial tissue according to any of paragraphs 30-38, wherein the basement membrane specimen or the basement membrane components-amorphous deposits specimen is obtained from a basement membrane or a basement membrane components-amorphous deposits prepared by culturing the cells having an ability to form a basement membrane in the presence of a matrix metalloproteinase (paragraph 39); the process for producing a reconstituted artificial tissue according to any of paragraphs 30-39, wherein the basement membrane specimen or the basement membrane components-amorphous deposits specimen is obtained from a basement membrane or a basement membrane components-amorphous deposit prepared by culturing a basement membrane component and/or growth factor hyperexpressing cells into which one or more types of genes and/or growth factors of basement membrane components are transfected (paragraph 40).

The present invention also relates to: a reconstituted artificial tissue which can be obtained by the production process according to any of paragraphs 30-40 (paragraph 41); the reconstituted artificial tissue according to paragraph 41, wherein the reconstituted artificial tissue is an artificial blood vessel, an artificial lung, an artificial liver, an artificial kidney, an artificial skin or an artificial cornea (paragraph 42); the reconstituted artificial tissue according to paragraph 41 or 42, wherein the reconstituted artificial tissue is an artificial human tissue (paragraph 43); the reconstituted artificial tissue according to any of paragraphs 41-43, which is detached from a support structure (paragraph 44); a method for testing the safety and toxicity of a test substance wherein the reconstituted artificial tissue according to any of paragraphs 41-44 is used (paragraph 45).

The artificial tissue prepared by the present invention 3 has a barrier function original to the living body since it has cell layers and a basement membrane structure with a barrier function original to the living body, aid can be advantageously applied as a tissue model to a pharmacological test, toxicity test and the like for chemical products. However, a support structure supporting an artificial tissue and a basement membrane specimen is formed in the condition of adhering to plastic surface, therefore it cannot be used as a regenerative medical material in such adhering condition, and its basement membrane structure will be broken if such a support structure is mechanically detached from plastic surface and it cannot be used as a tissue having physiological activity such as a barrier function original to the living body. It was, however, found that if a protein support structure is temporarily adhered to plastic surface through an adsorptive polymer by hydrophobic bonding having a hydrophobic linear carbon skeleton and a functional group which can react with protein in a molecule such as an alternating copolymer of methyl vinyl ether and maleic anhydride, and then an artificial tissue or a basement membrane specimen is formed on such a protein support structure supporting an artificial tissue or a basement membrane specimen can be physically detached from plastic surface when desired, and such a protein support structure supporting the detached artificial tissue and basement membrane specimen can be transplanted while maintaining the basement membrane structure. Thus the present invention 4 has been completed.

The present invention 4 relates to: a basement membrane specimen or an artificial tissue which is formed on a protein support structure temporarily adhered to plastic surface through an adsorptive polymer by hydrophobic bonding having a hydrophobic linear carbon skeleton and a functional group which can react with protein in a molecule (paragraph 46); the basement membrane specimen or the artificial tissue according to paragraph 46, wherein the adsorptive polymer by hydrophobic bonding is an adsorptive polymer by hydrophobic bonding shown by the following general formula [I] (paragraph 47):

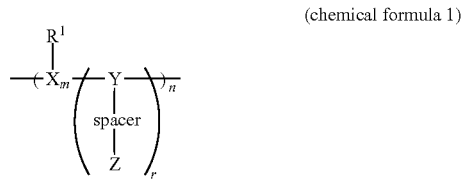

(chemical formula 1)

(In the formula, X denotes CH or NHCHCO, Y denotes CH or NHCR$^2$CO, R$^1$ denotes H, alkyl group of C1-C3, alkoxy group of C1-C3 or aryl group of C6-C8, R$^2$ denotes H or alkyl group of C1-C3, Z denotes a functional group (reactional group) optionally bonded to each other, spacer denotes (—CH$_2$—)p or (—NHCHR$^3$HCO—)q, R$^3$ denotes H or alkyl group of C1-C3, m denotes an integral number greater or equal to 1, n denotes an integral number between 100 and 20000, p and q independently denote 0 or integral numbers 1-8, r denotes an integral number greater or equal to 1); the basement membrane specimen or the artificial tissue according to paragraph 47, wherein the adsorptive polymer by hydrophobic ending shown by the general formula [I] is an alternating copolymer of methyl vinyl ether and maleic anhydride (paragraph 48); the basement membrane specimen or the artificial tissue according to any of paragraphs 46-48, wherein the basement membrane specimen is a basement membrane specimen constructed by removing the cells having an ability to form a basement membrane adhered onto a protein support structure through a basement membrane using a solvent having the ability to lyse lipid of the cells and an alkaline solution (paragraph 49); the basement membrane specimen or the artificial tissue according to any of paragraphs 46-49, wherein the artificial tissue is an artificial tissue prepared by culturing the cells having an ability to form a basement membrane on a protein support structure (paragraph 50); the basement membrane specimen or the artificial tissue according to any of paragraphs 46-50, wherein the artificial tissue is an artificial tissue prepared by culturing the cells having an ability to form a basement membrane on a protein support structure with a sugar-chain coat which can localize a receptor having an activity to accumulate a basement membrane component onto the basal surface of the cells having an ability to form a basement membrane (paragraph 51); the basement membrane specimen or the artificial tissue according to any of paragraphs 46-51, wherein the protein support structure is a collagen gel wherein fibroblasts are embedded (paragraph 52); the basement membrane specimen or the artificial tissue according to any of paragraphs 46-49, wherein the artificial tissue is an artificial tissue prepared by culturing the cells having an ability to form a basement membrane in the presence of a matrix metalloproteinase (paragraph 53); the basement membrane specimen or the artificial tissue according to any of paragraphs 46-53, wherein the artificial tissue is an artificial tissue prepared by culturing a basement membrane component and/or growth factor hyperexpressing cells into which one or more types of genes and/or growth factors of basement membrane components are transfected (paragraph 54); the basement membrane specimen or the artificial tissue according to any of paragraphs 46-49, wherein the artificial tissue is a reconstituted artificial tissue prepared by seeding and culturing the cells having certain ability to form a basement membrane on a basement membrane specimen paragraph 55); the basement membrane specimen or the artificial tissue according to any of paragraphs 46-55, wherein the cells having an ability to form a basement membrane are epithelial cells or endothelial cells (paragraph 56); the basement membrane specimen or the artificial tissue according to any of paragraphs 46-56, wherein the artificial tissue is an artificial epidermal tissue, an artificial corneal epithelial tissue, an artificial alveolar epithelial tissue, an artificial respiratory epithelial tissue, an artificial renal glomerular tissue, an artificial hepatic parenchymal tissue or an artificial pulmonary arterial vascular endothelial tissue, or, an artificial blood vessel, an artificial lung, an artificial liver, an artificial kidney, an artificial skin or an artificial cornea (paragraph 57).

The present invention 4 also relates to: a process for producing a basement membrane specimen or an artificial tissue which can be transplanted while maintaining the structure of a basement membrane wherein a protein support structure is temporarily adhered to plastic surface through an adsorptive polymer by hydrophobic bonding having a hydrophobic linear carbon skeleton and a functional group which can react with protein in a molecule, and a basement membrane specimen or an artificial tissue is formed thereon, and a protein support structure supporting a basement membrane specimen or an artificial tissue is physically detached from plastic surface when desired (paragraph 58); the process for producing a basement membrane specimen or an artificial tissue which can be transplanted while maintaining the structure of a basement membrane according to paragraph 58, wherein the adsorptive polymer by hydrophobic bonding is an adsorptive polymer by hydrophobic bonding shown by the following general formula [I] (paragraph 59):

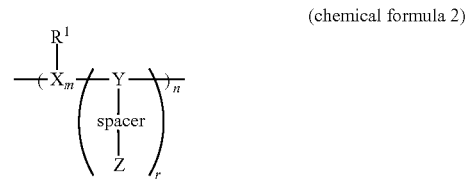

(chemical formula 2)

(In the formula, X denotes CH or NHCHCO, Y denotes CH or NHCR$^2$CO, R$^1$ denotes H, alkyl group of C1-C3, alkoxy group of C1-C3 or aryl group of C6-C8, R$^2$ denotes H or alkyl group of C1-C3, Z denotes a functional group (reactional group) optionally bonded to each other, spacer denotes (—CH$_2$—)p or (—NHCHR$^3$HCO—)q, R$^3$ denotes H or alkyl group of C1-C3, m denotes an integral number greater or equal to 1, n denotes an integral number between 100 and 20000, p and q independently denote 0 or integral numbers 1-8, r denotes an integral number greater or equal to 1); the process for producing a basement membrane specimen or an artificial tissue which can be transplanted while maintaining the structure of a basement membrane according to paragraph 59, wherein the adsorptive polymer by hydrophobic bonding shown by the general formula [I] is an alternating copolymer of methyl vinyl ether and maleic anhydride (paragraph 60); the process for producing a basement membrane specimen or an artificial tissue which can be transplanted while maintaining the structure of a basement membrane according to any of paragraphs 58-60, wherein the basement membrane specimen is a basement membrane specimen constructed by removing the cells having an ability to form a basement membrane adhered onto a protein support structure through a basement membrane using a solvent having the ability to lyse lipid of the cells and an alkaline solution (paragraph 61); the process for producing a basement membrane specimen or an artificial tissue which can be transplanted while maintaining the structure of a basement membrane according to any of paragraphs 58-61, wherein the artificial tissue is a basement membrane prepared by culturing the cells having an ability to form a basement membrane on a protein support structure (paragraph 62); the process for producing a basement membrane specimen or an artificial tissue which can be transplanted while maintaining the structure of a basement membrane according to any of paragraphs 58-62, wherein the artificial tissue is an artificial tissue prepared by culturing the cells having an ability to form a basement membrane on a protein support structure with a sugar-chain coat which can localize a receptor having an activity to accumulate a basement membrane component onto the basal surface of the cells having an ability to form a basement membrane (paragraph 63); the process for producing a basement membrane specimen or an artificial tissue which can be transplanted while maintaining the structure of a basement membrane according to any of paragraphs 58-63, wherein the artificial tissue is a reconstituted artificial tissue prepared by seeding and culturing the cells having a certain ability to form a basement membrane on the basement membrane specimen (paragraph 64); the process for producing a basement membrane specimen or an artificial tissue which can be transplanted while maintaining the structure of a basement membrane according to any of paragraphs 58-64, wherein the cells having an ability to form a basement membrane are epithelial cells or endothelial cells (paragraph 65); the process for producing a basement membrane specimen or an artificial tissue which can be transplanted while maintaining the structure of a basement membrane according to any of paragraphs 58-65, wherein the protein support structure is a collagen gel wherein fibroblasts are embedded (paragraph 66); the process for producing the basement membrane specimen or the artificial tissue which can be transplanted while maintaining the structure of a basement membrane according to any of paragraphs 58-66, wherein the artificial tissue is an artificial epidermal tissue, an artificial corneal epithelial tissue, an artificial alveolar epithelial tissue, an artificial respiratory epithelial tissue, an artificial renal glomerular tissue, an artificial hepatic parenchymal tissue or an artificial pulmonary arterial vascular endothelial tissue, or, an artificial blood vessel, an artificial lung, an artificial liver, an artificial kidney, an artificial skin or an artificial cornea (paragraph 67).

BEST MODE OF CARRYING OUT THE INVENTION

As for the method for preparing a basement membrane of the present invention 1, there is no particular limitation as long as it is a method wherein the cells having an ability to form a basement membrane are cultured on a protein support structure with a specific sugar-chain coat, namely a sugar chain which can localize a receptor having an activity to accumulate a basement membrane component on the basal surface of the cells having an ability to form a basement membrane. The above-mentioned cells having an ability to form a basement membrane can be exemplified by epithelial cells, endothelial cells, mesenchymal cells and the like. The above-mentioned epithelial cells can be more particularly exemplified by epidermal cells, corneal epithelial cells, alveolar epithelial cells, mucosal epithelial cells of digestive organ system, renal glomerular epithelial cells, hepatic parenchymal cells and the like, the above-mentioned endothelial cells can be more particularly exemplified by renal glomerular capillary endothelial cells, pulmonary arterial vascular endothelial cells, placental venous vascular endothelial cells, or aortic endothelial cells and the like, and the mesenchymal cells can be more particularly exemplified by muscle cells, adipocytes, glial cells, Schwann cells and the like.

A basement membrane component such as laminin, type IV collagen, heparan sulfate proteoglycan (HSPG), entactin or the like is required for the preparation of a basement membrane, and respective cells having an ability to form a basement membrane secret basement membrane components. The basement membrane components secreted from such cells, however, are secreted from the basal surface (lower surface) of the cells toward the inside of extracellular matrices formed by fibrous collagen matrix. Therefore, most of the secreted basement membrane components are apart from the basal surface, and they diffuse from the basal surface into a culture medium, or they are degraded by proteases in mid course, as a result, usually they are not effectively utilized. However, in the method for preparing a basement membrane of the present invention 1, an endogenous basement membrane component secreted from cells having an ability to form a basement membrane such as the above-mentioned epithelial cells, endothelial cells and the like can be more effectively utilized by culturing the cells having an ability to form a basement membrane on a protein support structure with a specific sugar-chain coat, namely a sugar chain which can localize a receptor having an activity to accumulate a basement membrane component to the basal surface of the cells having an ability to form a basement membrane.

Figure 3:
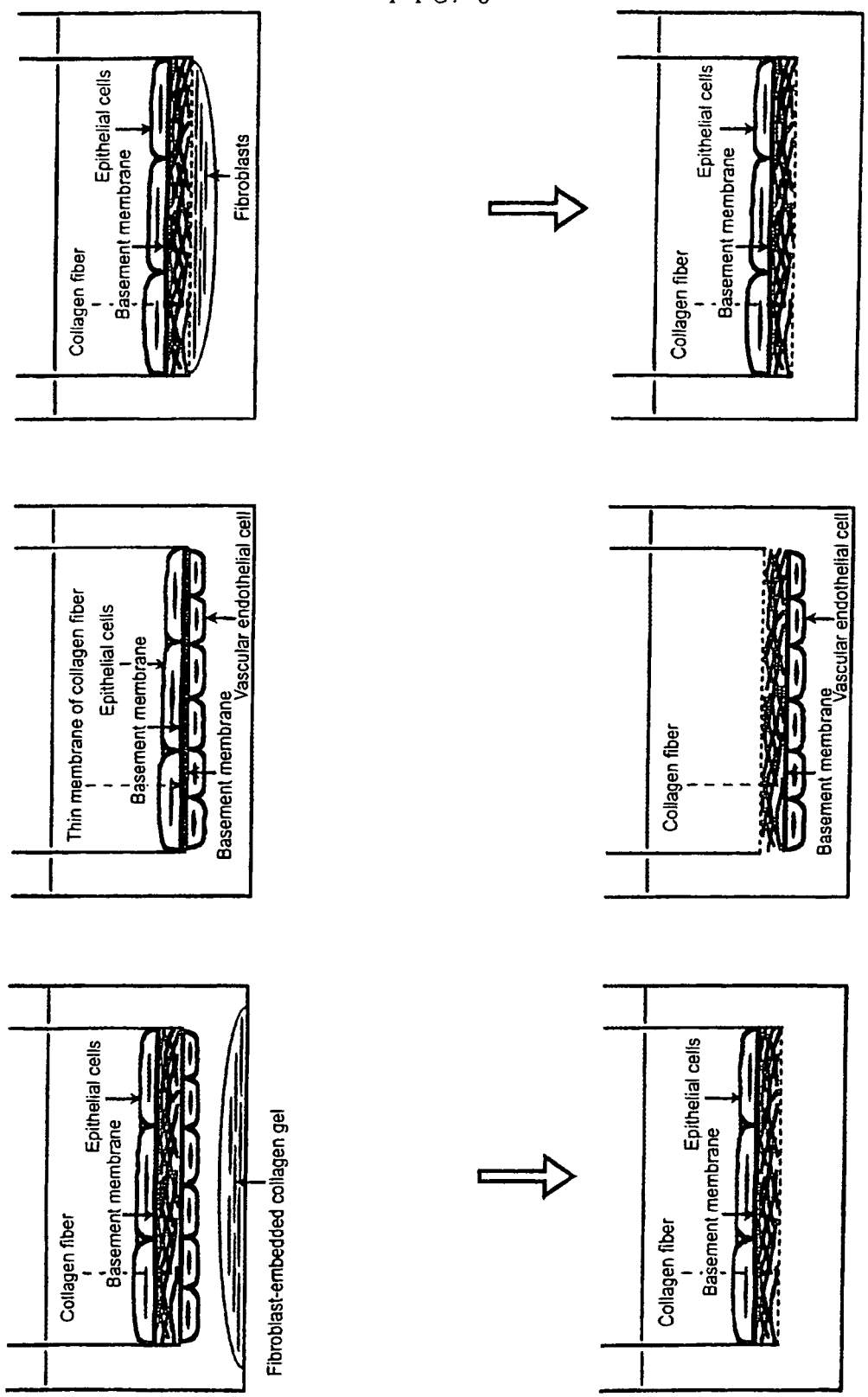
FIG. 3 is a set of schematic diagrams showing the formation of a basement membrane by the coculture of epithelial cells and endothelial cells.

Further, if the method for present invention 1 for culturing the cells having an ability to form a basement membrane is conducted on the two opposite basal surface of the protein support structure with sugar-chain coat, for example, if fibrous collagen is generated on the both sides of porous membrane, two types of cells having an ability to form a basement membrane such as the combination of epithelial cells and vascular endothelial cells and the like are seeded and cultured on its both sides, the diffusion of endogenous basement membrane components secreted from the cells having an ability to form a basement membrane is prevented, so that effective utilization of basement membrane components can be enhanced. In other words, the basement membrane components secreted from the cells on one side reaches to the other cells positioned on the opposite side of fibrous collagen, and is blocked by the barrier without a gap due to the cell-cell junction (tight junction) formed by such cells, and do not diffuse into culture medium, and as a result, the effective utilization of basement membrane components can be chanced. The upper stand of FIG. 3 schematically shows the following: the formation of a basement membrane by the coculture of epithelial cells and vascular endothelial cells through collagen fiber in the presence of fibroblasts embedded in collagen gel (left); the formation of a basement membrane by the coculture of epithelial cells and vascular endothelial cells through a thin membrane of collagen fiber which is a support structure with the sugar-chain coat of the present invention (middle); the formation of a basement membrane by the coculture of epithelial cells and fibroblasts through collagen fiber (right). Further, the lower stand of FIG. 3 shows the conditions wherein the cell tissues which are not needed such as a vascular endothelial tissue (left), epithelial tissue (middle), fibroblasts (right) are mechanically exfoliated. As for the combination of these cells, the following combinations are considered: epithelial cells and vascular endothelial cells; epithelial cells and epithelial cells; endothelial cells and endothelial cells; epithelial cells or endothelial cells and some mesenchymal cells, etc. The above-mentioned support structure can be exemplified by porous PET membrane, elastin (polymer) membrane, as well as fibrous collagen membrane, fibrous collagen matrix.

Further, in the method for preparing a basement membrane of the present invention 1, in order that a basement membrane can be prepared in the short term using even exogenous basement membrane components in addition to endogenous basement membrane components secreted from these cells having an ability to form a basement membrane, it is also possible to coculture with fibroblasts secreting basement membrane components and TGF-β, or more preferably with conditioned culture medium of fibroblasts or a fibroblast substitute such as Matrigel richly containing basement membrane components. Besides, in order that a basement membrane can be prepared in the short term in the same manner, it is also possible to culture the cells having an ability to form a basement membrane in the presence of one or more types of basement membrane components separately prepared such as laminin, type IV collagen, heparan sulfate proteoglycan (HSPG), entactin aid the like, or in the presence of TGF-β. As for the above-mentioned laminin and HSPG, commercially available products can be used, and as for type IV collagen, the one extracted using acetic acid from bovine lens capsule can be advantageously used.

Instead of the above-mentioned method wherein a basement membrane component such as laminin, type IV collagen, heparan sulfate proteoglycan (HSPG), entactin and the like, or TGF-β as mentioned above is used, which costs highly, a basement membrane component hyperexpressing cells into which genes of one or more types of basement membrane components such as laminin, type IV collagen and the like are transfected, or the growth factor hyperexpressing cells wherein the TGF-β genes are transfected can be selectively used as the cells having an ability to form a basement membrane and fibroblasts used for the method for preparing a basement membrane of the present invention 1. Particularly, a basement membrane specimen having a specific function can be obtained using the cells biosynthesizing and secreting a single molecular species of a basement membrane component by the gene manipulation.

As for the specific sugar chain for the method for preparing a basement membrane of the present invention 1, namely, the sugar chain which can localize a receptor having an activity to accumulate a basement membrane component onto the basal surface of the cells having an ability to form a basement membrane, it is preferable to use a sugar chain which can adhere the cells having an ability to form a basement membrane onto a support structure by the bonding of the sugar chain or a part of the sugar chain and the above-mentioned receptor, particularly a sugar chain wherein the sugar chain or a part of the sugar chain bonded to the receptor can be replaced by the above-mentioned basement membrane component. As for the support structure with a sugar chain of the present invention, it is preferable to be an integral molding body having a sugar chain, or a support structure coated with polymer having a sugar chain. The polymer having such sugar chain can be exemplified by a polymer having a sugar chain having β-D-glucopyranosyl nonreducing end or 2-acetoamide-2-deoxy-β-D-glucopyranosyl nonreducing end. Further, the polymer having a sugar chain having the β-D-glucopyranosyl nonreducing end can be particularly exemplified by PV-CA, PV-Lam and the like, and the polymer having a sugar chain having the 2-acetoamide-2-deoxy-β-D-glucopyranosyl nonreducing end can be particularly exemplified by a polymer macromolecule wherein oligosaccharides are introduced into a vinyl monomer such as PV-GlcNAc and the like (PV-sugar). The mixture of more than one types of these PV-sugars can also be used as well as a single type independently, and these PV-sugars are commercially available.

The support structure (with a sugar-chain coat) for the method for preparing a basement membrane of the present invention 1 can be exemplified by a fibrous collagen matrix, porous PET membrane, polystyrene plate, (synthetic) elastin polymer, bioabsorbable polymer and the like, however, a fibrous collagen matrix is more preferable in terms of maintaining the diffusion of nutritive salts and waste products. As for the fibrous collagen matrix, high density matrix of collagen gel contracted by fibroblasts can also be used. In this case, it is also possible to add ascorbic-2-phosphate (Asc-P) in order to enhance the synthesis of collagen. Further, a fibrous collagen matrix, which is constructed by leaving a neutral type I collagen solution at rest in $CO_2$ incubator to incubate it, and air-drying a resulting polymerized gel at room temperature, can also be used. It is preferable to use a bioabsorbable polymer since it is possible to transplant while maintaining the basement membrane structure supported by a support structure. Said bioabsorbable polymer can be particularly exemplified by polyglycolic acid, poly-L-lactic acid, L-lactic acid/glycol acid copolymer, glycol acid/ε-caprolactone copolymer, L-lactic acid/ε-caprolactone copolymer, poly-ε-caprolactone and the like.

As for the tissue model of the present invention 1, there is no particular limitation as long as it is a tissue containing cell layers which can be obtained by the method for preparing a basement membrane of the above-mentioned present invention and a basement membrane beneath the cell layers. For example, it can be particularly exemplified by epidermal tissue model, corneal epithelial tissue model, alveolar epithelial tissue model, respiratory epithelial tissue model, renal glomerular tissue model, hepatic parenchymal tissue model, pulmonary arterial vascular endothelial tissue model and the like. The tissue model of the present invention 1 has a barrier function original to a living body since it has a cell layer and a basement membrane structure same as those of a living body, therefore, it can be advantageously used particularly for applying to pharmacological test and toxicity test of chemical substances and the like compared to conventional artificial skin and the like which does not maintain barrier function. For example, it is possible to test the safety and toxicity of a test substance against an epithelial tissue by letting a test substance present onto the cell layer of an epithelial tissue model and measuring the electric resistance between the upper surface and the basal surface of the epithelial cells. The safety and toxicity of a test substance can be evaluated since electric resistance lowers if the test substance caused a lesion, even it is a minor one, to an epithelial tissue. It is also possible to test the safety and toxicity of a test substance against an epithelial tissue by letting a test substance present onto the cell layer of an epithelial tissue model, and monitoring the condition of the epithelial tissue and a basement membrane using a scanning electron microscope or a transmission electron microscope.

Figure 4:
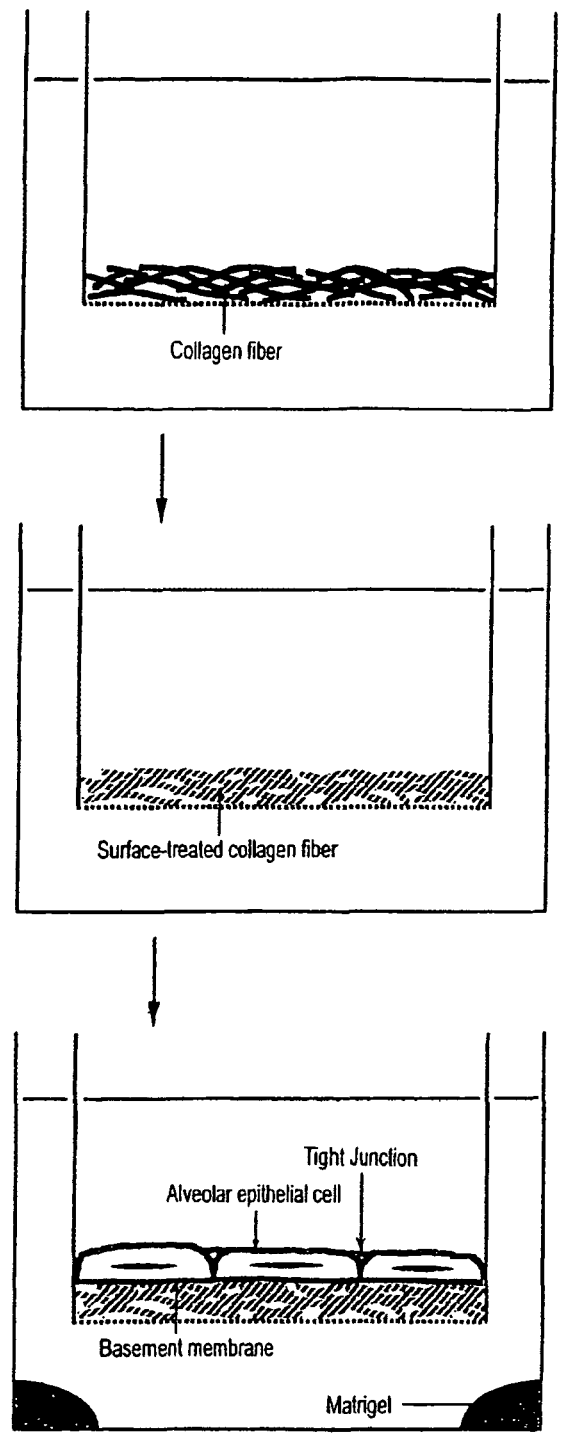
FIG. 4 is a set of schematic diagrams showing the construction of a basement membrane and the constitution of an alveolar epithelial tissue.

As for the test tissue kit of the present invention 1, there is no particular limitation as long as it is a kit containing a tissue model which can be obtained by the method for preparing a basement membrane of the present invention 1, for example, it can be exemplified by a test kit for pharmacological test, toxicity test and the like containing the tissue model structure of the present invention 1, and a tissue model construction kit for pharmacological test, toxicity test and the like. The tissue model construction kit can be particularly exemplified by a kit containing the following: certain cells comprising a test tissue; en extracellular matrix such as a fibrous collagen and the like coated with PV-GlcNAc and the like wherein said cells are seeded; a standard culture medium such as DMEM culture medium and the like for culturing the above-mentioned cells; Matrigel, type IV collagen solution, buffer solution and the like as a supplemental component. The course of the construction of a test tissue using said tissue model construction kit is shown in FIG. 4.

A basement membrane specimen (rBM; reconstructed basement membrane) can be further constructed from the tissue model of the present invention 1 by removing the cells having an ability to form a basement membrane from a basement membrane. Although there is no limitation to the method for removing the cells having an ability to form a basement membrane from a basement membrane, the method for removing epithelial cells and endothelial cells without damaging the basement membrane is preferable, and it is not preferable to remove the cells using a protease such as trypsin and the like, since the basement membrane itself will also be degraded. The method for removing epithelial cells and endothelial cells without damaging the basement membrane can be exemplified by a known method wherein the cells which formed a basement membrane such as alveolar epithelial cells and the like are treated with 0.18 M of hydrogen peroxide for 10 minutes, the culture was continued for 1 day thereafter, and cells are automatically detached from the basement membrane, however, the method for constructing a basement membrane specimen of the present invention 2 is preferable.

As for the method for constructing a basement membrane specimen of the present invention 2, there is no particular limitation as long as it is the method wherein the cells having an ability to form a basement membrane adhered onto a support structure through a basement membrane are removed using a solvent having the ability to lyse lipid of said cells and alkaline solution, however, the method wherein the treatment to remove proteinous and nucleic residues is conducted using alkaline solution after or at the same time as the delipidating treatment using a solvent having the ability to lyse lipid is preferable. The basement membrane specimen used herein means a basement membrane having a function to control morphology, differentiation, proliferation, motility, function expression and the like of cells when a desired homogenous or heterogeneous cells having an ability to form a basement membrane are seeded and cultured, and the above-mentioned cells having an ability to form a basement membrane can be exemplified by epithelial cells, endothelial cells, mesenchymal cells and the like. Further, the above-mentioned epithelial cells can be more particularly exemplified by epidermal cells, corneal epithelial cells, alveolar epithelial cells, mucosal epithelial cells of digestive organ system, renal glomerular epithelial cells, hepatic parenchymal cells and the like, and the above-mentioned endothelial cells can be more particularly exemplified by renal glomerular capillary endothelial cells, pulmonary arterial vascular endothelial cells, placental venous vascular endothelial cells, aortic endothelial cells etc., and the mesenchymal cells can be more particularly exemplified by muscle cells, adipocytes, glial cells, Schwann cells and the like. The above-mentioned cells having an ability to form a basement membrane which are adhered onto a support structure through the above-mentioned basement membrane includes a tissue which is an aggregate of said cells, preferably an artificial tissue of human and the like. As for said artificial tissue (tissue model), though there is no particular limitation as long as it is a tissue containing cell layers and a basement membrane beneath them, it can be particularly exemplified by epidermal tissue model, corneal epithelial tissue model, alveolar epithelial tissue model, respiratory epithelial tissue model, renal glomerular tissue model, hepatic parenchymal tissue model, pulmonary arterial vascular endothelial tissue model and the like.

There is no particular limitation to the solvent having the ability to lyse lipid of the above-mentioned cells, as long as it is a solvent which can possibly lyse lipid of epithelial cells and endothelial cells such as a surface active agent, organic solvent and the like, however, a surface active agent such as Triton X-100, Lubrol PX, deoxycholic acid, cholic acid, Tween, emulgen and the like is preferable, and among them Triton X-100 is particularly preferable. As for the concentration in use of the solvent that has the ability to lyse lipid such as a surface active agent and the like, for example, in the case of Triton X-100, 0.01-1.0%, or particularly around 0.1% is preferable, although it depends on the type of cells applied and the treatment time. There is no particular limitation to the above-mentioned alkaline solution, as long as it is an alkaline solution which dissolves the proteins remained on the basement membrane surface of the cells but does not dissolve the protein on the basement membrane, however, the alkaline solution with pH 8-14, or particularly, with pH 9-10 is preferable. The particular examples of such alkaline solution include an alkaline solution such as 20-50 mM of $NH_3$, 1 mM of NaOH or the like.

Besides, in order to suppress the degradation of a basement membrane by endogenous protease activity such as protease of DNase I and the like in lysosomes being liberated when the cells are lysed, a method which is conducted in phosphate buffer wherein protease inhibitor, or preferably, protease inhibitors cocktail (PIC) is added is preferable. Further, in the method for constructing a basement membrane specimen of the present invention, it is possible to conduct a pretreatment for the cells having an ability to form a basement membrane adhered to a support structure through a basement membrane such as an artificial human tissue and the like with vanadium salt such as 2 mM of $Na_3VO_4$ and the like in advance. If vanadium salt is used for pretreatment, cells will be easily exfoliated from a basement membrane, however, it is necessary to wash the vanadium salt.

Figure 1:
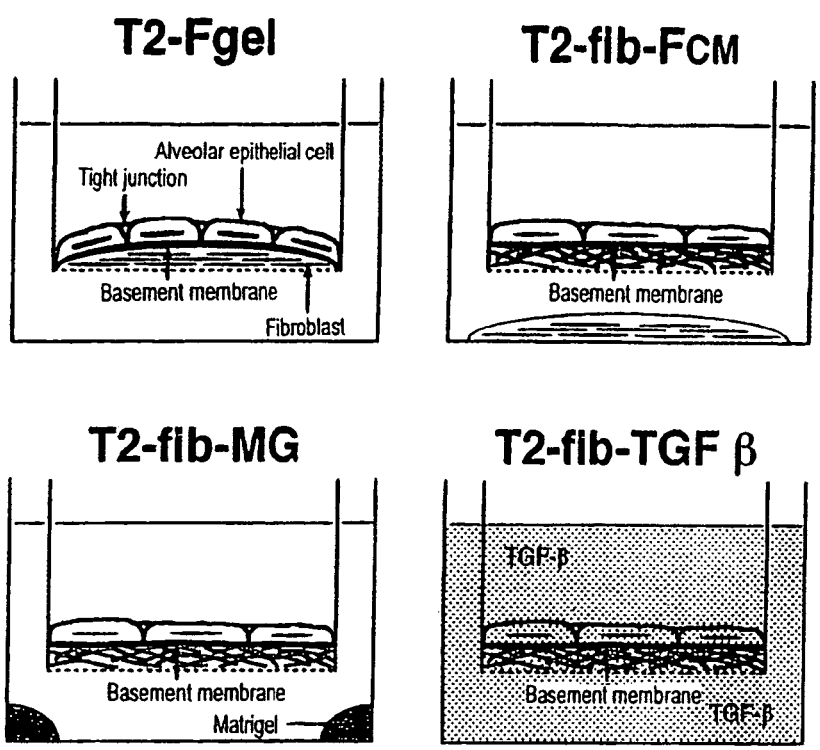
FIG. 1 is a set of schematic diagrams showing the formation of a basement membrane by alveolar epithelial cells.

As for the method for preparing the cells having an ability to form a basement membrane adhered onto a support structure through a basement membrane used in the construction of a basement membrane specimen of the present invention 2, such as, preferably, an artificial tissue of human and the like, the examples include a known method for preparing an artificial tissue as well as the method for preparing a basement membrane of the present invention 1. Such known method for preparing an artificial tissue can be eligibly exemplified by the following as shown in FIG. 1: the method for preparing an artificial tissue wherein epithelial cells are cultured on a pulmonary fibroblasts-embedded collagen matrix in upper well of culture insert (T2-Fgel); the method for preparing an artificial tissue wherein epithelial cells are cultured on fibrous collagen substratum in upper well in the presence of a pulmonary fibroblasts-embedded collagen matrix in lower well (T2-fib-Fcm); the method for preparing an artificial tissue wherein epithelial cells are cultured on a fibrous collagen substratum in upper well in the presence of Matrigel coat in lower well (T2-fib-MG); the method for preparing an artificial tissue wherein epithelial cells are cultured on a fibrous collagen substratum in upper well in the presence of growth factor TGF-β in upper well and lower wells (T2-fib-TGFβ. As shown FIG. 2, it can also be eligibly exemplified by the method for preparing a new artificial tissue wherein endothelial cells are cultured on a pulmonary fibroblasts embedded collagen gel in upper well of culture insert (EC-Fgel).

Other examples of the method for preparing a basement membrane include methods for increasing the supplied amounts of basement membrane components such as: the method for supplying the lacking basement membrane component from cocultured cells Cell Struc. Func., 22, 603-614, 1997); the method wherein a basement membrane component is added directly to culture system (J. Cell Sci., 113:859-868, 2000); the method for promoting the biosynthesis and secreting amount of a basement membrane component in the cells forming a basement membrane by adding growth factor to culture solution (Eur. J. Cell Biol., 78:867-875, 1999); the method wherein the basement membrane-component overexpressing cells or the growth factor overexpressing cells into which the genes of a basement membrane component or growth factor are transfected are used.

It can be further exemplified by the method for preparing an artificial tissue in the short term wherein the degradation of a basement membrane component is suppressed and basement membrane formation is accelerated using a matrix metalloproteinase (MMP) inhibitor. The cells forming a basement membrane secrete a plurality of matrix metalloproteases (MMP) which degrade basement membrane components as well as biosynthesize and secrete basement membrane components. Usually, a basement membrane is not formed by the cells independently since the degradation of basement membrane components by MMPs is larger than the secreted amount of the components necessary for basement membrane formation, however, if MMPs activities are suppressed, the basement membrane can be formed even with the small amount of secreted basement membrane components since the cells can effectively use the basement membrane components which was secreted by themselves for basement membrane formation. Such MMP inhibitors can be exemplified by the synthetic MMP inhibitors of the following: genetically manipulated products of synthesized TIMP (tissue inhibitor of Metalloproteinase); GM6001 (Calbiochem); MMP-2/MMP-9 inhibitor I (Calbiochem), CGS27023A (N-hydroxy-2-[[(4-methoxyphenyl)sulfonyl]3-pycolyl]amino)-methyl butane amido hydrochloride) (J. Med. Chem. 1997, Vol. 40, p. 2525-2532); MMP inhibitor (p-NH2-Bz-Gly-Pro-D-Leu-D-Ala-NHOH) (FN-439) (BBRC, 1994, Vol. 199, p. 1442-1446), Batimastat (BB-94) (J. Med. Chem. 1998, Vol. 41, p. 1209-1217) and the like. As for the method for constructing the basement membrane wherein these MMP inhibitors are used, for example, the basement membrane and the like can be formed by seeding the cells having an ability to form a basement membrane such as alveolar epithelial cells and the like onto the culture matrix such as fibrous collagen and the like, adding MMP inhibitor in 100-1,000-fold amount of $IC_{50}$ (inhibitor concentration for lowering the enzyme activity to 50%) against MMP-2 rich is one of MMP, and culturing for 10 days to 2 weeks.

As for the basement membrane specimen of the present invention 2, there is no particular limitation as long as it can be obtained by the method for constructing the basement membrane specimen of the above-mentioned present invention 2, and such basement membrane specimen wherein epithelial cells, endothelial cells and the like are exfoliated, and the basement membrane is exposed, for example, the above-mentioned basement membrane specimen comprised of the basement membrane structure formed by epithelial cells, endothelial cells and the like and a support structure such as collagen fiber and the like can be advantageously used for the process for producing a reconstituted artificial tissue of the present invention 3. Although the basement membrane cannot be stored in the condition that the cells are attached, the basement membrane specimen of the present invention 2 comprised exclusively of non-cell composition as a result that the cells are removed has a merit of being easy to be stored, and can be used at any time and any place when needed. Moreover, the basement membrane specimen can be stored under refrigeration or in freezer without any problem.

Other aspects of the basement membrane specimen of the present invention include a basement membrane specimen in a free state from a support structure. By directly transplanting a basement membrane specimen without a plastic membrane and the like, or the basement membrane specimen of the present invention which is not fixed to plastic surface, for example, a basement membrane specimen formed on collagen fiber, to an affected part, cells having an ability to form a basement membrane are proliferated on a basement membrane specimen, and tissue and the like in the affected part can be constituted in vivo. The process for producing the basement membrane of the present invention 4 can be advantageously applied for the instruction of the above-mentioned basement membrane specimen without a plastic membrane and the like.

There is no particular limitation to the process for producing the reconstituted artificial tissue of the present invention 3, as long as it is a method for seeding and culturing certain cells having an ability to form a basement membrane on a basement membrane specimen or an amorphously basement membrane components-deposited specimen. The cells having an ability to form a basement membrane with the different origin of a basement membrane specimen or an amorphously basement membrane components-deposited specimen (hereinafter referred to as "the basement membrane specimen and the like") can also be used in the same manner as the cells having an ability to form a basement membrane with the same origin as the basement membrane specimen and the like. The above-mentioned cells having an ability to form a basement membrane can be exemplified by epithelial cells, endothelial cells, mesenchymal cells and the like. The above-mentioned epithelial cells can be more particularly exemplified by epidermal cells, corneal epithelial cells, alveolar epithelial cells, mucosal epithelial cells of digestive organ system, renal glomerular epithelial tissue, hepatic parenchymal cells and the like, the above-mentioned endothelial cells can be more particularly exemplified by renal glomerular capillary endothelial cells, pulmonary arterial vascular endothelial cells, placental venous vascular endothelial cells, or aortic endothelial cells and the like, and the mesenchymal cells can be more particularly exemplified by muscle cells, adipocytes, glial cells, Schwann cells and the like. As for the above-mentioned reconstituted artificial tissue (tissue model), preferably a reconstituted artificial human tissue (human tissue model), there is no particular limitation as long as it is a tissue or an organ of human and the like containing cell layers and a basement membrane beneath them. For example, it can be particularly exemplified by epidermal tissue model, corneal epithelial tissue model, alveolar epithelial tissue model, respiratory epithelial tissue model, renal glomerular tissue model, hepatic parenchymal tissue model, pulmonary arterial vascular endothelial tissue model and the like.

As for the basement membrane specimen and the like used for the process for producing reconstituted artificial tissue of the present invention 3, there is no particular limitation as long as it is a specimen of a basement membrane or a basement membrane component amorphous deposit (hereinafter referred to as "the basement membrane and the like") having a function to control morphology, differentiation, proliferation, motility, function expression and the like of cells when desired homogenous or heterogeneous cells having an ability to form a basement membrane are seeded and cultured thereon. The term "the basement membrane components-amorphous deposits specimen" used herein means the incomplete basement membrane comprised of amorphous structure irregularly containing basement membrane components and the like wherein secreted material of the cells are deposited and accumulated beneath the cells, and which has an equal or less function to control morphology, differentiation, proliferation, motility, function expression and the like of cells compared to the case of the above-mentioned basement membrane when desired homogenous or heterogeneous cells having an ability to form a basement membrane are seeded and cultured thereon. There is no particular limitation to the method for constructing the basement membrane and the like including the above-mentioned known method such as to treat with hydrogen peroxide solution and the like. However, it can be particularly eligibly exemplified by the method for constructing a basement membrane specimen of the present invention, namely a method for constructing a basement membrane specimen wherein the cells having an ability to form a basement membrane which are adhered onto support structure through a basement membrane are removed using a solvent having the ability to lyse lipid of said cells and an alkaline solution, preferably a method for constructing a basement membrane specimen wherein the treatment to remove proteinous and nucleic residues using an alkaline solution is conducted after or at the same time as the delipidating treatment using solvent having the ability to lyse lipid.

Other aspects of the artificial tissue of the present invention 3 can be exemplified by the method for culturing the cells having an ability to form a basement membrane on the opposite two substratum surfaces of a support structure. For example, a fibrous collagen is constructed on the both sides of porous membrane, two types of cells having an ability to form a basement membrane such as a combination of epithelial cells and vascular endothelial cells and the like are seeded and cultured on the both sides, then the diffusion of endogenous basement membrane components secreted from the cells having an ability to form a basement membrane is prevented, and as a result, the effective utilization of a basement membrane component can be enhanced. As for the combination of these cells, the following combinations are considered: epithelial cells and vascular endothelial cells; epithelial cells and epithelial cells; endothelial cells and endothelial cells; epithelial cells or endothelial cells and some mesenchymal cells, and the like.

Figure 5:
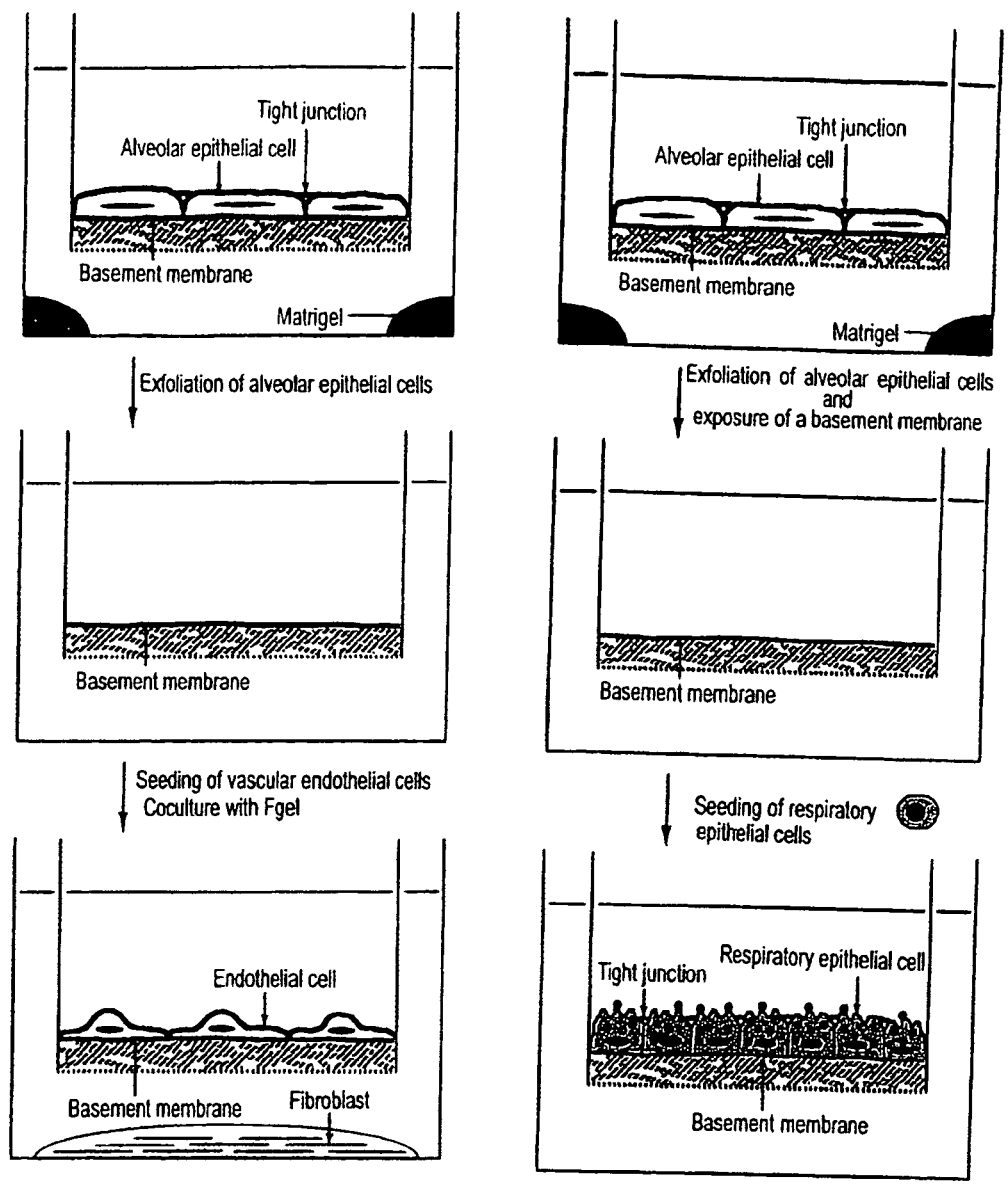
FIG. 5 is a set of schematic diagrams showing the constitution of an endothelial tissue and an epithelial tissue using a reconstituted basement membrane specimen.

According to the present invention 3, the above-mentioned basement membrane specimen and the like wherein epithelial cells and endothelial cells we exfoliated, aid a basement membrane aid the like is exposed such as a basement membrane specimen comprised of a basement membrane structure formed by epithelial cells and endothelial cells and the like, and a fibrous support structure such as collagen fiber and the like can be used for the culture of other cells (see FIG. 5). Although the basement membranes of epithelium and of endothelium are not same, most of their components are common, and the basement membrane formed by epithelial cells can be used to the constitution of endothelial cells. For example, human epithelial tissue or human endothelial tissue can be reconstituted simply by seeding and culturing the aimed human epithelial cells or human endothelial cells on the basement membrane specimen. Actually, it has been confirmed that pulmonary arterial vascular endothelial tissue can be constituted by seeding and culturing pulmonary arterial vascular endothelial cells on the basement membrane formed by type II alveolar epithelial cells. It is preferable to let interstitial cells (fibroblasts) of the aimed organs or tissues cocultured when epithelial cells or vascular endothelial cells are seeded on the basement membrane specimen to form a new epithelial or endothelial tissue since the basement membrane formation and maintenance in the new tissue will be smoothly conducted by the aid of the interstitial cells.

As mentioned above, the reconstitution method for epithelial cells and endothelial cells wherein a basement membrane specimen and the like is utilized have a high versatility, and for example, the basement membrane constituted using rat alveolar epithelial cells can be used for the reconstitution of a human tissue, moreover, organs and tissue reconstituted from basement membrane derived from such rat alveolar epithelial cells are not limited to alveolus. In contrast, in the case that epithelial tissue, endothelial tissue and the like are constituted by forming a basement membrane through the culture of epithelial cells and endothelial cells of respective organs, it takes much time and work to develop the culturing system corresponding to respective cells, and it incurs a lot of waste to separately prepare the basement membrane for respective tissues. As mentioned above, however, it is possible to construct efficiently the reconstituted artificial tissue of the present invention 3 using the basement membrane specimen as a common base material for tissue reconstitution. Further, there is no particular limitation to the culture vessel for the case of reconstituting epithelial tissue, endothelial tissue and the like by utilizing the basement membrane specimen, it can be applied to hollow fiber method as well as culture insert method. When it is applied to an artificial blood vessel, for example, it can avoid the development of thrombus, which is a problem in artificial blood vessel, and when applied to dialysis treatment, it can reduce the burden of patients.

As mentioned above, both of the tissue model and the organ model of the present invention 3 which are reconstituted from a basement membrane specimen and the like can also be advantageously applied to pharmacological test and toxicity test of chemical substances since they are equipped with barrier function original to a living body because they contain cell layers and a basement membrane structure with barrier function original to a living body in the same manner as a conventional tissue model. For example, it is possible to test the safety and toxicity of a test substance against an epithelial tissue by letting a test substance present onto the cell layer of an epithelial tissue model and measuring the electric resistance between the apical surface and the basal surface of the epithelial cells. The safety and toxicity of a test substance can be measured since electric resistance lowers if the test substance caused a lesion, even it is a minor one, to an epithelial tissue. It is also possible to test the safety and toxicity of a test substance against an epithelial tissue by letting a test substance present onto the cell layer of an epithelial tissue model, and monitoring the condition of the epithelial tissue and a basement membrane using a scanning electron microscope or a transmission electron microscope.

Moreover, the basement membrane specimen without plastic membrane and the basement membrane specimen which is not fixed on plastic surface, for example, a tissue and an organ and the like reconstituted by utilizing the basement membrane specimen formed on fibrous collagen matrix have much higher versatility since they can be transplanted while maintaining the basement membrane structure. Their application examples include artificial microvessel with the inside diameter less than or equal to 3 mm, and human implantable artificial tissue and the like. They can be particularly eligibly exemplified by a tissue and an organ with which epithelial cells and endothelial cells exist contiguously such as artificial glomerulus, artificial liver, artificial alveolus and the like. As for the construction of the above-mentioned basement membrane specimen without a plastic membrane, the process for producing the basement membrane specimen of the present invention 4 can be advantageously applied. For example, when tissue and organs and the like are constituted by utilizing a basement membrane specimen formed on fibrous collagen matrix, a basement membrane specimen can be easily and mechanically exfoliated from plastic membrane and plastic surface according to need without any fear that a basement membrane specimen is exfoliated from plastic membrane during the operation after the culture and to lose their value in use.

As for the basement-membrane-specimen or the artificial tissue of the present invention 4, there is no particular limitation as long as it is a basement membrane specimen or an artificial tissue formed on the protein support structure temporarily adhered to plastic surface through an adsorptive polymer by hydrophobic bonding having a hydrophobic linear carbon skeleton and a functional group which can react with protein in a molecule. Besides, as for the process for producing the basement membrane specimen or the artificial tissue which can be transplanted while maintaining the structure of a basement membrane of the present invention, there is no particular limitation as long as it is a method comprising the steps of; temporarily adhering the protein support structure onto plastic surface through an adsorptive polymer by hydrophobic bonding having a hydrophobic linear carbon skeleton and a functional group which can react with protein in a molecule, and letting a basement membrane specimen or an artificial tissue formed thereon, and physically exfoliating the protein support structure supporting a basement membrane specimen or an artificial tissue from plastic surface when desired. The above-mentioned adsorptive polymer by hydrophobic bonding is shown by the above-mentioned general formula [I] (in the formula, X denotes CH or NHCHCO, Y denotes CH or NHCR$^2$CO, R$^1$ denotes H, alkyl group of C1-C3, alkoxy group of C1-C3 or aryl group of C6-C8, R$^2$ denotes H or alkyl group of C1-C3, Z denotes a functional group (reactional group) optionally bonded to each other, spacer denotes (—CH$_2$—)p or (—NHCHR$^3$HCO—)q, R$^3$ denotes H or alkyl group of C1-C3, m denotes an integral number greater or equal to 1, n denotes an integral number between 100 and 20000, p and q independently denote 0 or integral numbers 1-8, r denotes an integral number greater or equal to 1). In such general formula [I], as for R$^1$, the alkyl group of C1-C3 can be exemplified by methyl group, ethyl group, n-propyl group, isopropyl group and the like, the alkoxy group of C1-C3 can be exemplified by methoxy group, ethoxy group, propoxy group, isopropoxy group and the like, and aryl group of C6-C8 can be exemplified by phenyl group, benzyl group, phenethyl group, phenoxy group, benzyloxy group, phenethyloxy group and the like. As for said adsorptive polymer by hydrophobic bonding, an adsorptive polymer by hydrophobic bonding having a hydrophobic linear skeleton such as polyvinyl chain, linear amino acid polymer (polyglycine, polyalanine, polyphenylalanine, tyrosine, etc.), and its derivatives in a molecular, such as an adsorptive polymer by hydrophobic bonding and the like which can be adsorbed to plastic surface, that has a reactive functional group (reactional group) which can directly react to said hydrophobic linear skeleton or react to protein support structure through a spacer can be eligibly used. The range of n in said general formula [I] is 100-20000, the molecular weight of adsorptive polymer by hydrophobic bonding shown by the general formula [I] is preferable to be around 15,000-3,200,000.

As for the above-mentioned reactional group, there is no particular limitation as long as it can react and bond to the functional group of protein support structure. Its examples include reactional group of carboxylic acid anhydride type, amino group, SH group and the like. The above-mentioned reactional group of carboxylic acid anhydride type can be eligibly exemplified by maleic anhydride which bonds to functional group such as N-terminal amino group, lysine ε-amino group, SH group and the like of protein. Although the above-mentioned amino group reacts to carboxyl group of protein, it is preferable to add a peptide-condensing agent for the chemical bonding. The above-mentioned SH group reacts mainly to SH group of protein, but it also bonds to S—S bonding in SS exchange reaction in some cases. Further it is also possible to attach a reversible protecting group which can be easily unset as long as the above-mentioned hydrophobic linear skeleton and copolymer can be formed on said SH group.

Said adsorptive polymer by hydrophobic bonding having the reactional soup can be exemplified by a copolymer of one or more types selected from: ethylene; unsaturated ether such as methyl vinyl ether, ethyl vinyl ether, ethyl-1-propenyl ether and the like; or α-amino acid and the like such as alanine, glycine, valine, leucine, isoleucine, phenylalanine, tyrosin and the like; and one or more types selected from: dicarboxylic acid or acid inside such as maleic anhydride, maleic anhydride imidate and the like; amino acid including sulfur such as lysine, cystein and the like; monoamino dicarboxylic acid such as aspartic acid, gultamic acid and the like; diamino monocarboxylic acid such as lysine and the like. These copolymer can be copolymers wherein dimmer, trimer and the like are bilaterally copolymerized, however, it is preferable to be an alternating copolymer. Further, in the case of amino acid including sulfur, monoamino dicarboxylic acid, diamino monocarboxylic acid and the like, these polymers have the structure with functional group in hydrophobic linear skeleton formed by condensation, therefore, they can be applied as an adsorptive polymer by hydrophobic bonding having functional group of the present invention 4. Among them, the adsorptive polymer by hydrophobic bonding having functional group of the present invention can be particularly exemplified by MMAC (methyl vinyl ether/maleic anhydride copolymer) which is an alternating copolymer of maleic anhydride and unsaturated ether such as methyl vinyl ether, ethyl vinyl ether, ethyl-1-propenyl ether and the like. In the case of MMAC and the like, linear polymer with methylene group as a skeleton makes it possible to adsorb to plastic surface by hydrophobic bonding, however, if it is only with —$CH_2$—$CH_2$— skeleton, it is too hydrophobic and its affinity to water will lower, and there will possibly be a disadvantage for reactivity as a result of microscopically repelling water. Therefore, regarding the one wherein some H atoms of methylene group are substituted with alkoxy group of C1-C3 or aryl group of C6-C8 as mentioned above, for example, regarding the one substituted with alkoxy group such as methoxy group, ethoxy group, propoxy group, isopropoxy group, and the like, phenoxy group, benzyloxy group, phenethyloxy group and the like, reaction efficiency is considered to be enhanced due to the presence of O atom. Besides, it is not preferable to substitute with OH group instead of alkoxy group since ester bonding with carboxylic acid anhydride is made between the molecules. MMAC is easier to use compared to the polymer which requires acetone and the like since it is ethanol-soluble, moreover, it can be air-dried quickly after sprayed. Further, as for the MMAC concentration when used for coating treatment of plastic surface as ethanol solution and the like, 2 μg/ml-1 mg/ml, or particularly, 10-50 μg/ml is eligible, and such coating treatment can be repeated for 1-3 times according to the desired level of temporary adhesion. Further, maleic anhydride which is a reactional group of MMAC is to bond to amino acid of protein such as collagen and the like, it can ionically bond to + electric charge of protein even if this maleic anhydride becomes carboxyl acid as a result of reacting to water.

Besides, the above-mentioned adsorptive polymer by hydrophobic bonding can adsorb to plastic surface irrespective of types or material of mastic since they adsorb to plastic surface by hydrophobic bonding not by chemical bonding due to their hydrophobic linear skeleton. If protein support structure is temporarily adhered to plastic surface through said adsorptive polymer by hydrophobic bonding, and artificial tissue or a basement membrane specimen is formed thereon, it is possible to physically exfoliate a protein support structure supporting an artificial tissue or abasement membrane specimen from plastic surface when desired, and it becomes also possible to transplant the protein support structure supporting the exfoliated artificial tissue or basement membrane specimen while maintaining the structure of a basement membrane. Further, the above-mentioned protein support structure can be eligibly exemplified by the one used for the present invention 1, the basement membrane specimen formed on the protein support structure can be eligibly exemplified by the basement membrane specimen of the present invention 2, and the artificial tissue (including artificial organ) of human and the like formed on the protein support structure can be particularly exemplified by the artificial tissue of the present invention 3, for example, particularly by an artificial tissue such as an artificial epidermal tissue, an artificial corneal epithelial tissue, an artificial alveolar epithelial tissue, an artificial respiratory epithelial tissue, an artificial renal glomerular tissue, an artificial hepatic parenchymal tissue or an artificial pulmonary arterial vascular endothelial tissue, or, an artificial organ such as an artificial blood vessel, an artificial lung, an artificial liver, an artificial kidney, an artificial skin, an artificial cornea and the like.

The present invention will be more particularly explained in the following with reference to the examples, but the technical scope of the invention will not be limited to these examples.

Example 1

Epithelial Cells, Endothelial Cells and the Like Forming a Basement Membrane

As for epithelial cells, type II alveolar epithelial cells (obtained from rats transfected with SV40-large T antigen genes; T2 cells) which were provided by Dr. A. Clement, Hôpital Armand Trousseau, Paris (Clement et al., Exp. Cell Res., 196: 198-205, 1991) were cultured in DMEM (Dulbecco's modified Eagle medium) wherein 10 mM of 2-[4-(2-hydroxyethyl)-1-piperazinyl]ethanesulfonic acid (HEPES) (pH 7.2), 10% fetal bovine serum (FBS; Hyclone Laboratories Inc., Logan, Utah), penicillin, and streptomycin are added, in the atmospheric condition of air 95%/$CO_2$ 5%, and used. As for endothelial cells, human pulmonary arterial vascular endothelial cells (HPAE cells) purchased from Clonetics were cultured in culture medium of MCDB 131 alone wherein 10 mM of HEPES (pH 7.2), 2% FBS, growth factor, penicillin, and streptomycin are added, or culture medium of equal mixture of MCDB 131 and DMEM, in the atmospheric condition of air 95%/$CO_2$ 5%, and used. As for fibroblasts, the one prepared from pulmonary fibroblasts derived from male rats Jcl: Fischer 344 according to the method previously described (CELL STRUCTURE AND FUNCTION 22: 603-614, 1997) and the human pulmonary fibroblasts purchased from Clonetics were used.

Example 2

Preparation of Fibrous Collagen Gel

Collagen gel fiber was prepared on the model of dense matrix of collagen gel usually constituted by fibroblasts. Type I neutral collagen solution in DMEM (pH 7.2) (0.3-0.5 mg/ml of type I collagen obtained from 0.42 ml of bovine dermis by acid extraction; Koken Co., Tokyo) were added to 4.3 $cm^2$ of cultured fibroblast layer together with polyethylene terephthalate ester membrane of 6-well culture plate (Becton Dickinson Labware, Franklin Lakes, N.J.), and incubated in $CO_2$ incubator for a few hours-24 hours, then allowed to gelling. This gel was air-dried aid compressed at room temperature for 24-48 hours, and used as high-density collagen fiber (fib). As for the above-mentioned fibroblasts, pulmonary fibroblasts derived from male rats Jcl: Fischer 344 were prepared according to the method previously described (CELL STRUCTURE AND FUNCTION 22: 603-614, 1997).

Example 3

Constitution of Tissue Model 1

Figure 2:
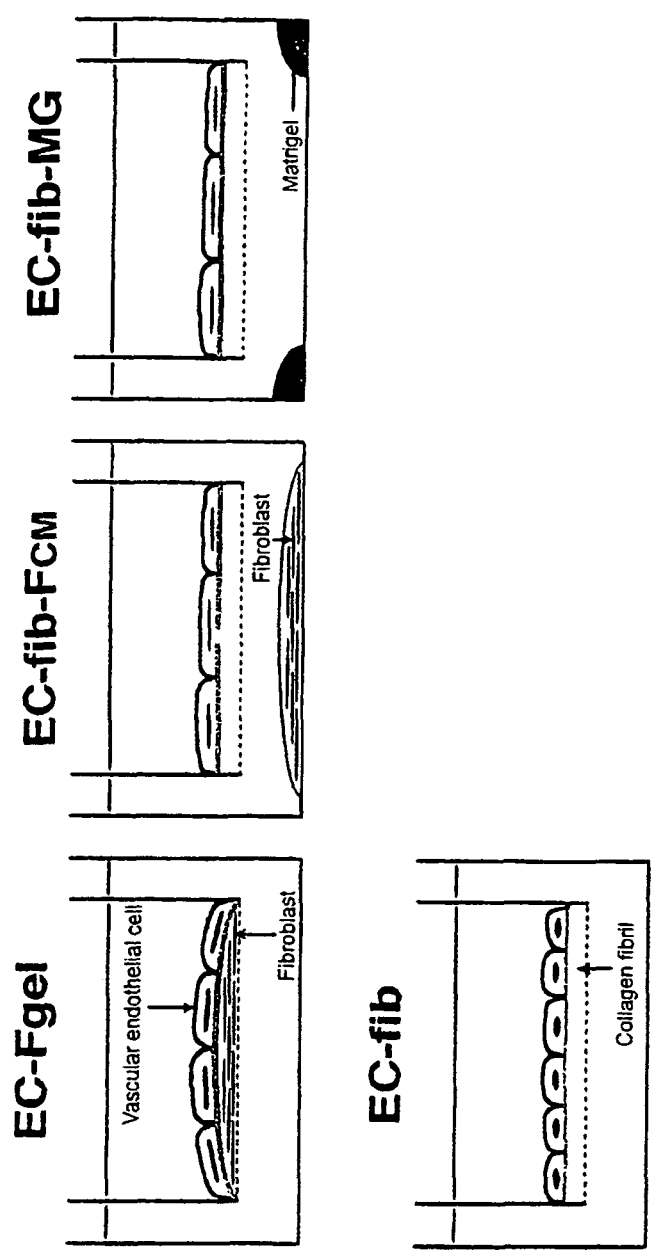
FIG. 2 is a set of schematic diagrams showing the formation of a basement membrane by pulmonary arterial vascular endothelial ells.

The methods for forming epithelial tissues and endothelial tissues having a basement membrane beneath the type II alveolar epithelial cells and vascular endothelial cell layers are shown in FIG. 1 and FIG. 2 respectively. In order to constitute most basic tissue model, the above-mentioned epithelial cells (T2) or endothelial cells (HPAEC) were seeded directly on the collagen gel wherein fibroblasts were embedded, and cultured for 2 weeks (T2-Fgel in FIG. 1, EC-Fgel in FIG. 2). Further, in order to form epithelial tissue and endothelial tissue having a basement membrane using the above-mentioned fib as culture matrix, epithelial cells (T2) or endothelial cells (HPAEC) were directly seeded on fib and cultured for 2 weeks (T2-fib-Fcm, T2-fib-MG and T2-fib-TGFβ in FIG. 1). In FIG. 1, Fcm shows the coculture with collagen gel wherein fibroblasts are embedded (Fgel), MG shows the culture wherein the bottom of culture plate is coated with Matrigel 200 μl (Becton Dickinson), and TGFβ shows the culture wherein 1 ng/ml of TGFβ is added.

Example 4

Figure 6:
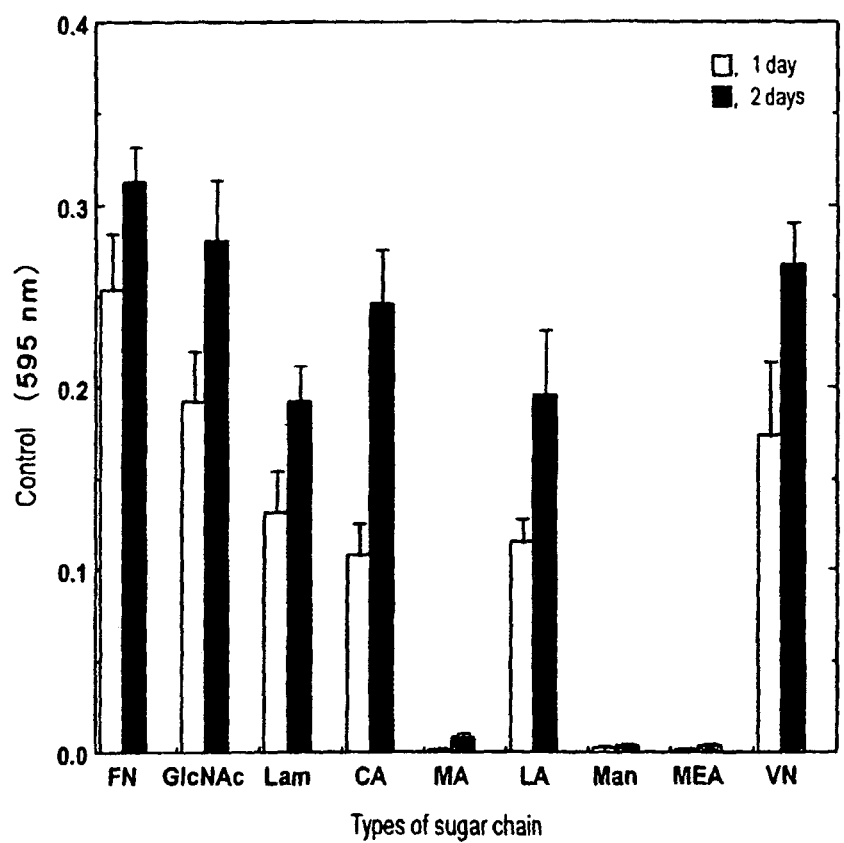
FIG. 6 is a drawing showing the adhesion specificity of type II alveolar cells on sugar chains.

Confirmation of the Presence of a Receptor in Epithelial Cells 96-well polystyrene plate (Becton Dickinson) were coated with various kinds of PV-sugars (Seikagaku Corporation) with 10 μg/ml concentration according to the protocol of the manufacturer, $1 \times 10^4$ of type II rat alveolar epithelial cells were seeded thereon, and incubated in DMEM wherein 10 mM HEPES (pH 7.2) and 1% FBS were added in $CO_2$ incubator at 37° C. for 24-48 hours. After the incubation, the cells were stained with crystal violet and the adhesiveness to various kinds of PV-sugars was investigated by measuring the absorbence of 595 nm and setting the same as cell number. Further, cell adhesion of cell adhesion factor against fibronectin (FN) and vitronectin (VN) coats were also conducted simultaneously as a control experiment. The results are shown in FIG. 6. The abscissa axis in FIG. 6 shows various kinds of PV-sugars of nonreducing end sugar chain (GlcNAc; 2-acetoamide-2-deoxy-β-D-glucopyranosyl, Lam; β-D-glucopyranosyl-(1→3), CA; β-D-glucopyranosyl-(1→4), LA; β-D-glucopyranosyl, MA; α-D-glucopyranosyl, Man; β-D-mannopyranosyl, MEA; α-D-galactopyranosyl). FIG. 6 shows that type II alveolar epithelial cells have strong adhesiveness to: PV-GlcNAc with sugar chain having 2-acetoamide-2-deoxy-β-D-glucopyranosyl nonreducing end; PV-CA or PV-Lam with sugar chain having β-D-glucopyranosyl nonreducing end; PV-LA with sugar chain having β-D-galactopyranosyl nonreducing end. These results show that type II alveolar epithelial cells express a receptor against these sugar chains on their basal surface.

Example 5

Constitution of Tissue Model 2; Preparation of a Basement Membrane by Type II Alveolar Epithelial Cells As for the preparation of a basement membrane, a culture insert comprised of a lower well, and an upper well which can be placed in said lower well on concentric circle and which has a PET membrane in its bottom was used (see FIG. 1). On the PET membrane at the bottom part of upper well, type II alveolar epithelial cells were cultured at 37° C. in the presence of 5% $CO_2$ for 2 weeks on the support structure (fib*) wherein high-density collagen fiber (fib) constructed by the method shown in Example 2 was coated with PV-GlcNAc, PV-CA or PV-Lam lysed in DMEM with concentration of 10 μg/ml. In this culture, collagen gel wherein fibroblasts are embedded (Fgel), Matrigel (MG), or TGFβ were not added to culture system, DMEM wherein 10 mM of HEPES (pH7.2), 1% FBS, and 0.2 mM of ascorbic acid-2-phosphate (Asc-P) were added was used for the culture solution. Transmission electron micrographs of an alveolar epithelial tissue thus formed are shown in FIG. 7, and scanning electron micrographs of extracellular matrices beneath an exposed alveolar epithelial tissue as a result of removing type II alveolar epithelial cell layers on the surface of an alveolar epithelial tissue thus formed cording to the method shown in Example 8 (to be hereinafter described) are shown in FIG. 8.

Figure 7:
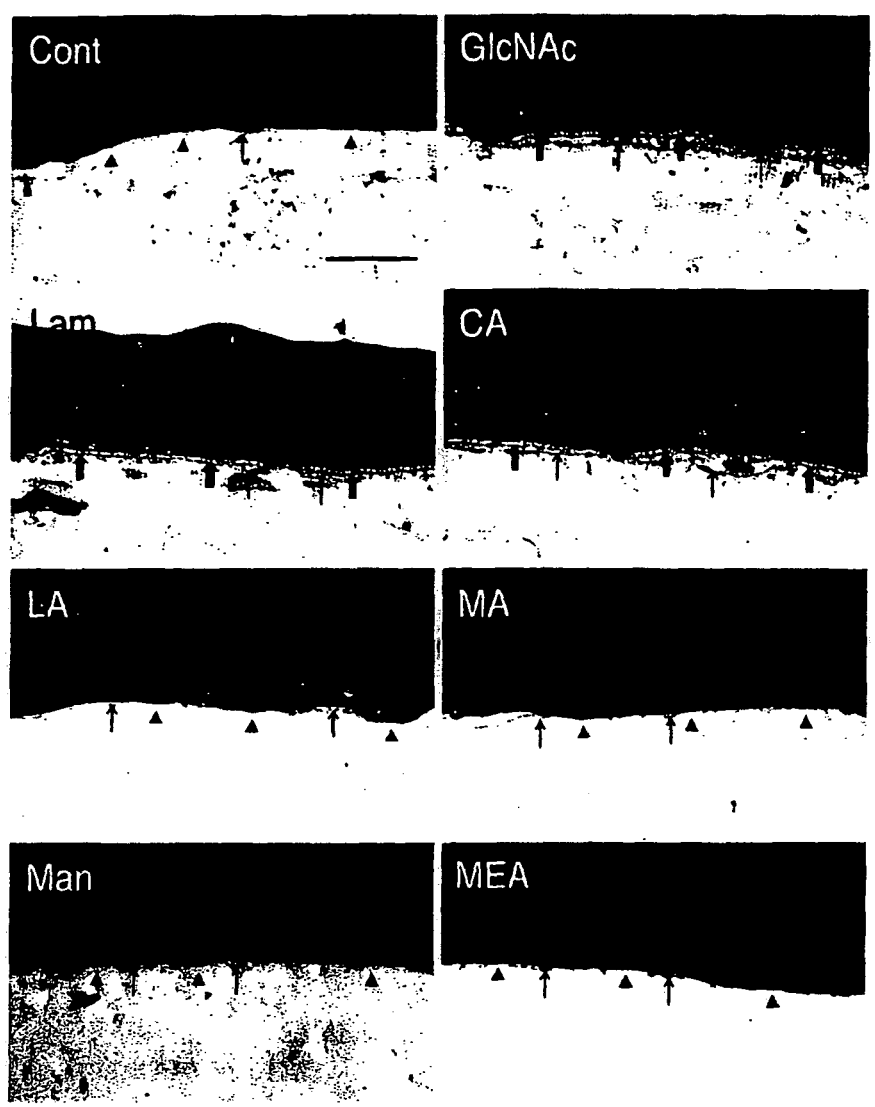
FIG. 7 is a set of transmission electron micrographs of an alveolar epithelial tissue formed as a result of 2-week culture of type II alveolar epithelial cells on the high density collagen fiber (fib*) coated with various kinds of PV-sugars.
Figure 8:
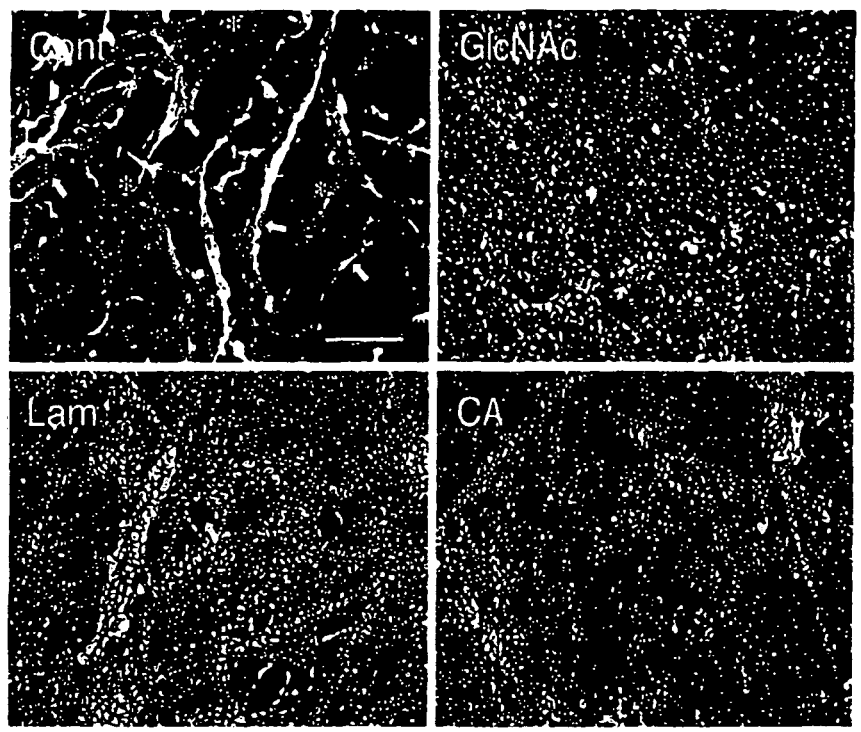
FIG. 8 is a set of scanning electron micrographs of extracellular matrices beneath an alveolar epithelial tissue formed as a result of 2-week culture of type II alveolar epithelial cells on the high density collagen fiber (fib*) coated with various kinds of PV-sugars.

In FIG. 7, the bold arrows show the basement membrane lamina densa, the small arrows show the old basement membranes which were formed at the beginning of the culture, and a part of which is being degraded, and the arrowheads show the regions wherein a basement membrane is not formed (scale length is 1 μm) respectively. Further, in the untreatment of PV-sugar (Cont) in FIG. 8, only the spots existing on fib (collagen fiber, outlined bold arrow) where secretion of epithelial cells are accumulated (*) were confirmed, but with treatment of PV-GlcNAc, PV-Lam or PV-CA, a basement membrane is flatly formed (in response to the bold arrows in FIG. 7), in PV-Lam treatment, lower part of collagen fiber (outlined bold arrow) are glimpsed from the defective window of a basement membrane part of which are lost when type II alveolar epithelial cell layer is removed (scale length is 1 μm). Based on these results, it has been confirmed that if the culture is conducted on high-density collagen fibrous support structure coated with PV-GlcNAc having 2-acetoamide-2-deoxy-β-D-glucopyranosyl nonreducing end, PV-CA or PV-Lam having β-D-glucopyranosyl nonreducing end (GlcNAc-fib*, CA-fib*, Lam-fib*), an alveolar epithelial tissue wherein a basement membrane is formed beneath type II alveolar epithelial cell layer is constituted. Further, although type II alveolar cells adhere to PV-LA having β-D-galactopyranosyl nonreducing end (FIG. 6), a basement membrane was not formed (FIGS. 7 and 8). This fact shows that cell adhesiveness to sugar chain is a necessary condition but not a sufficient condition for the formation of a basement membrane.

Example 6

The Acceleration Effect for a Basement Membrane Formation by Matrigel

Figure 9:
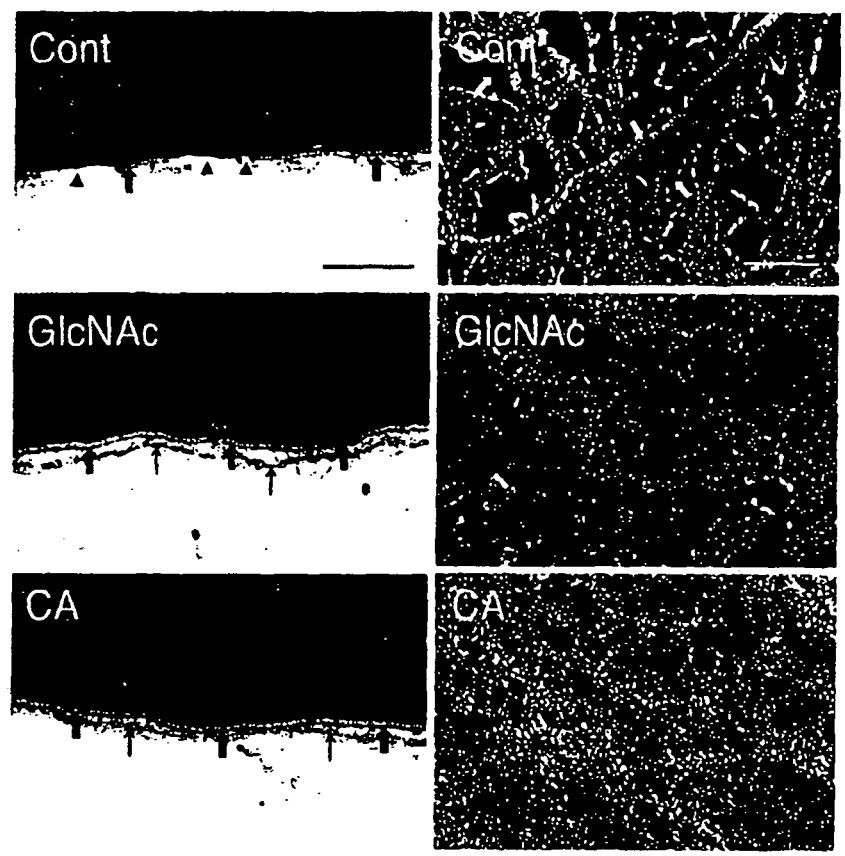
FIG. 9 is a set of transmission electron micrographs of an alveolar epithelial tissue (left) and scanning electron micrographs of extracellular matrices beneath an alveolar epithelial tissue (right), both of which were formed as a result of 10-day coculture of type II alveolar epithelial cells with 25 µl of Matrigel coat on the bottom face of a culture dish on the high density collagen fiber (fib*) coated with various kinds of PV-sugars.

As shown by T2-fib-MG in FIG. 1, when lower well are coated with Matrigel 200 μl, and alveolar epithelial cells are cultured on high-density collagen fiber (fib) for 2 weeks, a basement membrane is formed beneath epithelial cells. However, if the amount of Matrigel is less than 50 μl, a basement membrane is not formed (J. Cell Sci., 113:589-868, 2000). Even in this case, if high-density collagen fiber (fib) are constructed according to the method shown in Example 2, and culture matrix (fib*) coated with PV-GlcNAc, PV-CA or PV-Lam are used according to the method shown in Example 5, a basement membrane is formed beneath type II alveolar epithelial cell layer after the 10-days culture. FIG. 9 shows the transmission electron micrographs of an epithelial tissue (left side: untreated, and PV-GlcNAc, PV-CA coating) formed as a result of 10-days coculture with Matrigel 25 μl coating the bottom of culture plate on the high density collagen fiber (fib*) coated with various kinds of PV-sugars, and scanning electron micrographs (right side: untreated, and PV-GlcNAc, PV-CA coating) of the result of removing alveolar epithelial cell layers according to the method shown in Example 8 (to be hereinafter described) and exposing a basement membrane structure just beneath them to the surface (the meanings of the marks and scale are same as in Example 5). Based on these results, it has been confirmed that even if the amount of Matrigel is insufficient, alveolar epithelial tissues wherein a basement membrane is formed can be constituted just beneath type II alveolar epithelial cell layer using high-density collagen fibrous support structure coated with PV-GlcNAc or PV-CA (GlcNAc-fib*, CA-fib*).

Example 7

Figure 10:
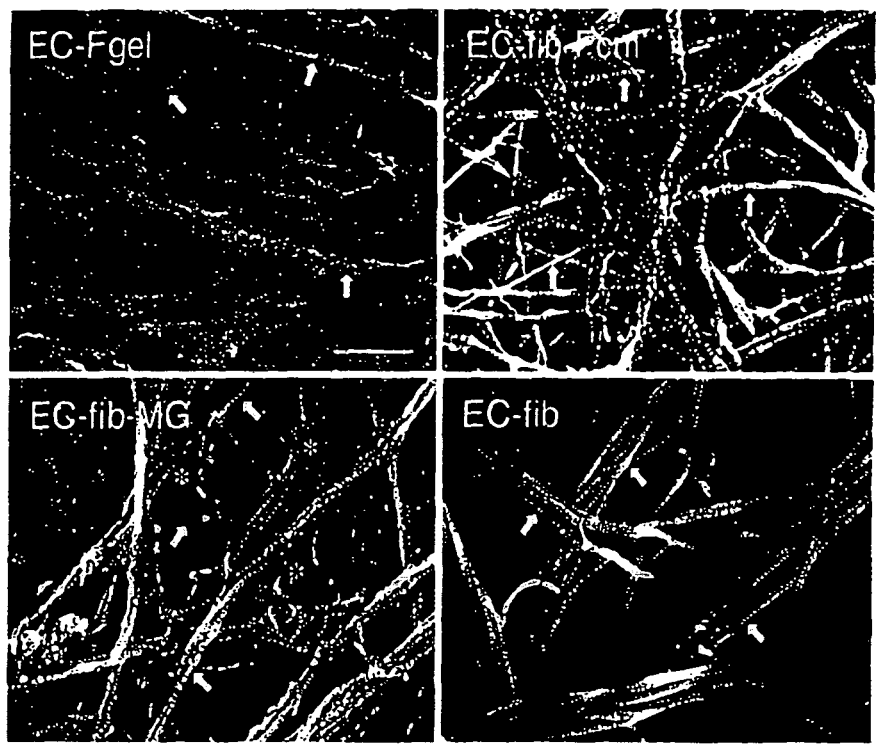
FIG. 10 is a set of scanning electron micrographs of extracellular matrices which show the result of basement membrane formation c human pulmonary arterial vascular endothelial cells by the culture method shown in FIG. 2.
Figure 11:
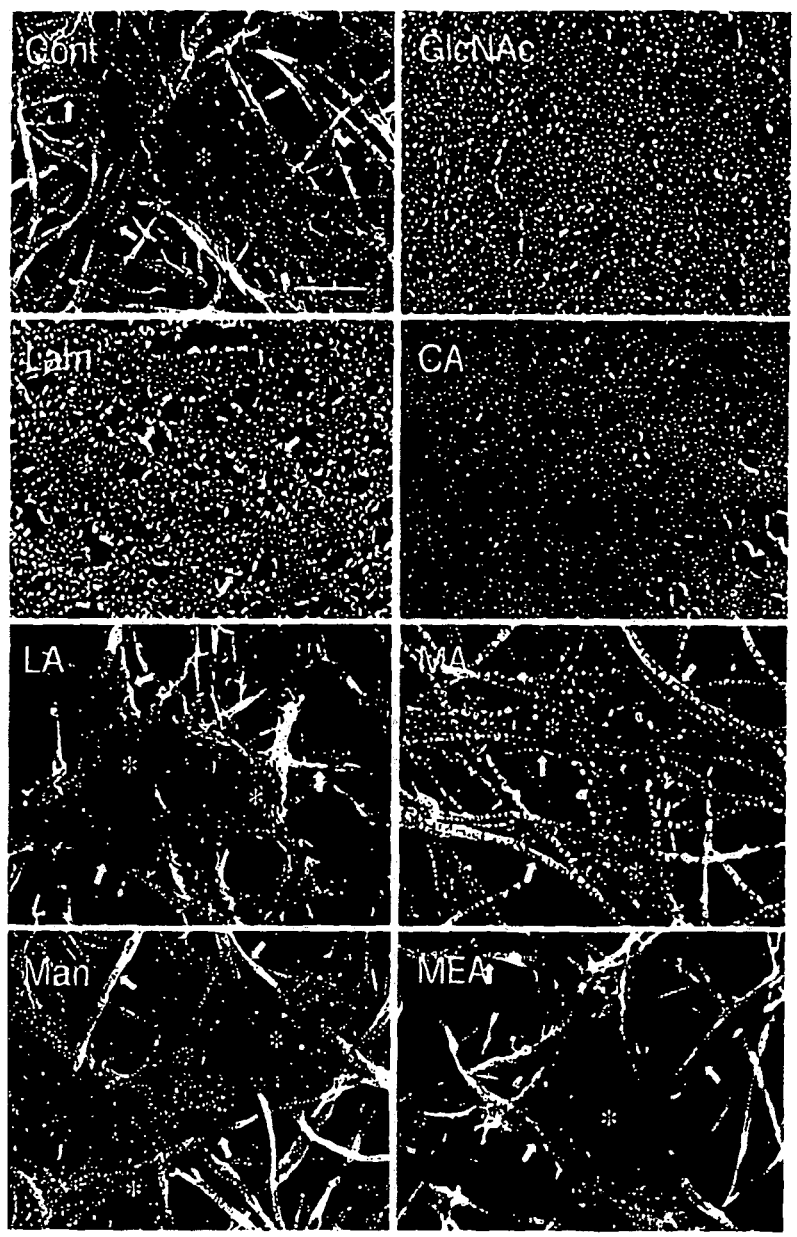
FIG. 11 is a set of scanning electron micrographs of extracellular matrices beneath vascular endothelial cell layers formed as a result of seeding human alveolar artery vascular endothelial cells on the high density collagen fiber (fib*) coated with various kinds of PV-sugars and coculturing for 2 weeks with a collagen gel wherein alveolar fibroblasts are embedded (EC-fib*-Fcm).

Preparation of a Basement Membrane by Human Pulmonary Arterial Vascular Endothelial Cells Human pulmonary arterial vascular endothelial (HPAE) cells were cultured according to the method shown in FIG. 2. More particularly, the culture was conducted in the following way: direct culture on the collagen gel wherein human fibroblasts are embedded (Fgel) (EC-Fgel); culture on high-density collagen fiber (fib) in the presence of Fgel (EC-fib-Fcm); coculture with 200 μl of Matrigel on fib (EC-fib-MG); culture on fib (EC-fib). After the culture, HPAE cell layer on the surface was removed according to the method for referential example 1 (to be hereinafter described), and extracellular matrix structure beneath the cells were monitored by scanning electron microscope (FIG. 10). Although a basement membrane was formed in the case of EC-Fgel, existing collagen fiber was exposed in the case of EC-fib-Fcm, EC-fib-MG, and EC-fib and a basement membrane was not formed as in the case of T2 cells (T2-fib-Fcm, T2-fib-MG) (the outlined bold arrows show collagen fiber. * shows secretion deposited between collagen fibers. Scale length is 1 μm). Accordingly, culture system of EC-fib-Fcm was used for the culture on high-density collagen fibrous support structure (fib*) coated with PV-sugar as in the case of type II alveolar epithelial cells of Example 5. After the culture, HPAE cell layer on the surface was removed according to the method for referential Example 1, extracellular matrix structure exposed just beneath the cells was monitored by scanning electron microscope (FIG. 11). In the case of PV-GlcNAc and PV-CA coating, formation of a basement membrane was confirmed. In the case of PV-Lam coating, the formation of a basement membrane was incomplete. In the case of PV-sugar untreated (Cont), and PV-LA, PV-MA, PV-Man, PV-MEA treatments, secretion of epithelial cells were accumulated (*) on the existing collagen fiber (outlined bold arrows), however, a basement membrane was not formed. Based on these results, it has been confirmed that if fib* coated with PV-GlcNAc, PV-CA (GlcNAc-fib*, CA-fib*) are used, human pulmonary arterial vascular endothelial tissue wherein a basement membrane is formed just beneath human pulmonary arterial vascular endothelial cell layer was constituted.

Example 8

Construction of a Basement Membrane Specimen Wherein an Alveolar Epithelial Cell Layer is Removed and a Basement Membrane is Exposed As schematically shown in FIG. 5, type II alveolar epithelial cell layer was exfoliated from tissue model (T2-fib-MG), a basement membrane specimen wherein a basement membrane is exposed was constructed, rat respiratory epithelial cells or human pulmonary arterial vascular epithelial cells were seeded on such constructed basement membrane structure, and respiratory epithelial tissue and vascular epithelial tissue were constructed. Firstly, 2 ml of 0.1% of Triton X-100 (surface active agent) in isotonic phosphate buffer (pH7.2; PBS (−)) containing protease inhibitors cocktail (PIC, Peptide Institute, Inc., Osaka) was used to lyse and elute the lipid components of epithelial cells of the type II alveolar epithelial tissue on a culture insert of upper well, and simultaneously, the procedure to lyse protein residues of the cells remained on the basement membrane surface with coexisting 50 mM of $NH_3$ was conducted. This procedure of Triton X-100 and $NH_3$ treatment was repeated twice (proteins of a basement membrane should not be lysed), then an alveolar epithelial cell layer was exfoliated from the basement membrane and the basement membrane specimen wherein a basement membrane is exposed was prepared, followed by another washing with PBC (−) solution containing PIC to remove surface active agent and alkaline solution.

Example 9

Figure 12:
FIG. 12 is a set of transmission electron micrographs of a respiratory epithelial tissue constituted on a reconstructed basement membrane specimen.
Figure 12:
Figure 12:

Reconstitution of Rat Respiratory Epithelial Tissue on the Basement Membrane Structure $5 \times 10^5$ of rat respiratory epithelial cells (SPOC1, provided by Dr. Paul Nettesheim of NIEHS (National Institute of Environmental Health and Sciences)) in United States were seeded on the basement membrane structure constituted in Example 8, and cultured at 37° C. in the presence of 5% $CO_2$ for 1 week in mixed culture medium, of Ham's F12:DMEM=1:1 wherein 10 mM of HEPES (pH 7.2) and 1% FBS were added, thus respiratory epithelial tissues were constituted. Transmission electron micrographs of respiratory epithelial tissue constituted on the basement membrane structure are shown in FIG. 12. FIG. 12A shows respiratory epithelial cells on the basement membrane structure, FIG. 12B shows the strongly magnified boundary surface of basal surface of respiratory epithelial cell and basement membrane structure wherein respiratory epithelial cells recognizing the basement membrane derived from alveolar epithelial cells are connected with an anchoring filament, FIG. 12C shows the formation of epithelial tissue by the bonding of respiratory epithelial cells with cell-cell junction.

Example 10

Figure 13:
FIG. 13 is a set of transmission electron micrographs (A-C) of a human vascular endothelial tissue constituted on a reconstructed basement membrane specimen.

Reconstitution of Human Vascular Epithelial Tissue on the Basement Membrane Structure $5\times10^5$ of human pulmonary arterial vascular endothelial cells (Clonetics) were seeded on the basement membrane structure constituted in Example 8, and cultured at 37° C. in the presence of 5% $CO_2$ for 2 weeks in mixed culture medium of MCDB131:DMEM=1:1 wherein 10 mM of HEPES (pH 7.2) and 2% FBS were added, thus human vascular endothelial tissue were constituted. Transmission electron micrographs of human vascular endothelial tissue constituted on the basement membrane structure are shown in FIG. 13. FIG. 13A shows human vascular epithelial tissue constituted as a result of coculture with fibroblasts, FIG. 13B shows human vascular epithelial tissue constituted in the presence of Matrigel.

Example 11

Figure 14:
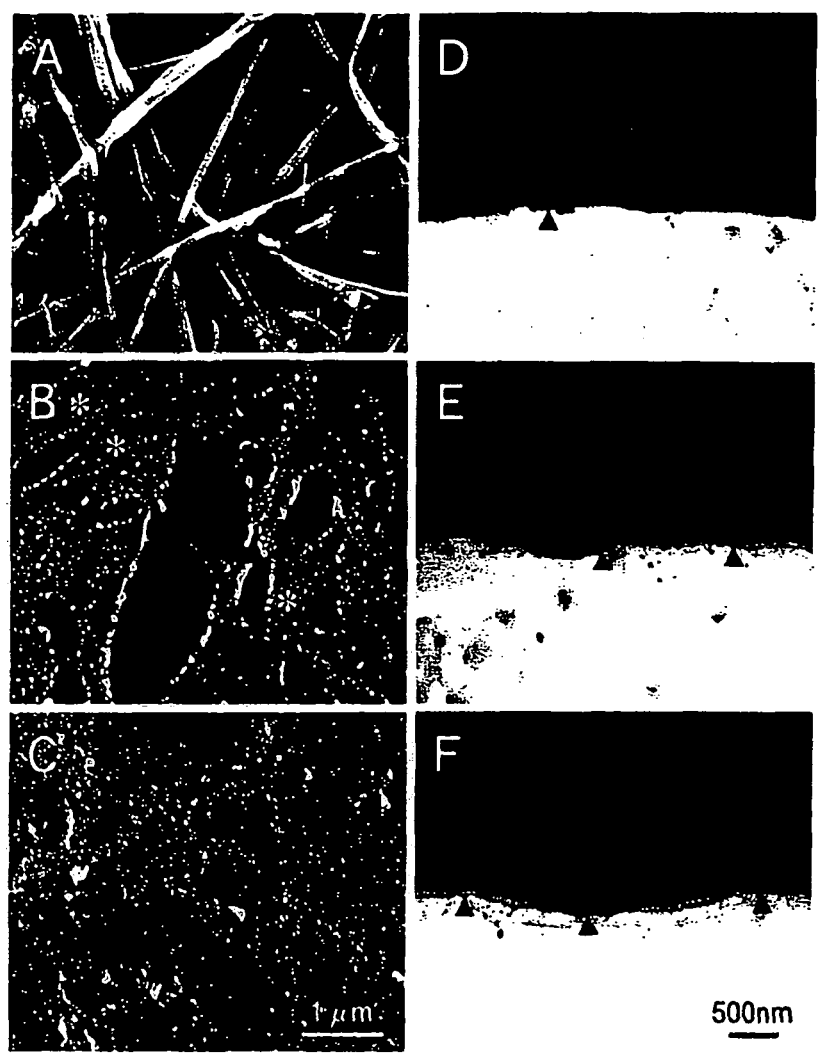
FIG. 14 is a set of scanning electron micrographs of collagen fiber (fib) (A), amorphous deposits structure (deposit—fib: shown with *) (B) and a reconstructed basement membrane-specimen (rBM) (C) wherein secreted deposits beneath the cells is exposed to the surface as a result of removing the cells after the culture of alveolar epithelial cells on a collagen fiber under the condition that a basement membrane is not formed and that a basement membrane is formed, and transmission electron micrographs (D-F) of type II alveolar epithelial tissue reconstituted thereon.

Construction of Amorphous Deposit Specimen of Basement Membrane Component and the Like Even in the case that a complete basement membrane was not formed by alveolar epithelial cells, basement membrane components secreted to outside from the cells deposited as in amorphous structure beneath the cells. It is possible to prepare secreted materials specimen which has become amorphous structure by selectively removing the cells, for example, in the condition of attaching to extracellular matrix such as collagen fiber and the like, or in the state of directly depositing on plastic surface, since the deposits comprised of extracellular matrices, growth factors and the like are used as a culture matrix. Type II alveolar epithelial cells (T2 cells) were seeded on high-density collagen fiber (fib), and cultured for 1 or 2 weeks (see the above-mentioned Example 1-3). After the culture of 1 or 2 weeks, alveolar epithelial cell layers were removed according to the method described in Example 8, and a basement membrane specimen and the like wherein in a basement membrane and the like were exposed was prepared. FIG. 14 A-C are the scanning electron micrographs respectively show the following: FIG. 14A shows collagen fiber (fib); FIG. 14B shows amorphous deposit structure (deposit—fib: shown with *) wherein secreted materials deposited under the cells are exposed to the surface as a result of removing the cells by culturing under the condition that a basement membrane is not formed; FIG. 14C shows the basement membrane structure (rBM) which is exposed to the surface as a result of removing the cells after the basement membrane is formed.

Example 12

Construction of Tissue Wherein Amorphous Deposit Specimen (Deposit—Fib) is Used-1

Aimed tissue can be constructed by seeding and culturing epithelial cells, endothelial cells, muscle cells, adipocytes, Schwann cells and the like on a basement membrane specimen (FIG. 14C) or amorphous deposit specimen (FIG. 14B). Although the performance and stability of the tissue formed when the cells of the aimed tissue are seeded on amorphous deposit are generally inferior compared to the case where they are seeded on a basement membrane specimen, they are remarkably superior in the performance when compared to the case where cells are seeded directly on the plastic or untreated extracellular matrix. Alveolar epithelial cells were seeded on collagen fiber (fib), amorphous deposit specimen (deposit—fib), and a basement membrane structure (rBM), and cultured for a short term (3 days). FIG. 14 D-F are the transmission electron micrographs respectively showing the following: FIG. 14D shows the result of culture on untreated collagen fiber (fib); FIG. 14E shows the result of culture on amorphous deposit specimen (deposit—fib); FIG. 14F shows the result of culture on a basement membrane structure (rBM). In the culture on untreated collagen fiber (fib), deposits of extracellular matrices beneath the cells (▲) is very little, and the formation of anchoring filament connecting the cells and a basement membrane is consequentially little. In the culture on the basement membrane structure (rBM), anchoring filament connecting basement membrane lamina densa (▲) and the basal surface of the cells is well formed, it can be seen that tissue is being formed as the cells are recognizing and accepting the basement membrane specimen as its own basement membrane. In the culture on amorphous deposit specimen (deposit—fib), as the deposit (▲) and the basal surface of the cells are partially connected by an anchoring filament, tissue formation is also incomplete compared to the case of the basement membrane structure (rBM), however, the formation of anchoring filament is further progressed compared to the case of untreated collagen fiber (fib).

Example 13

Construction of Tissue Wherein Amorphous Deposit Specimen (Deposit—Fib) is Used-2

Figure 15:
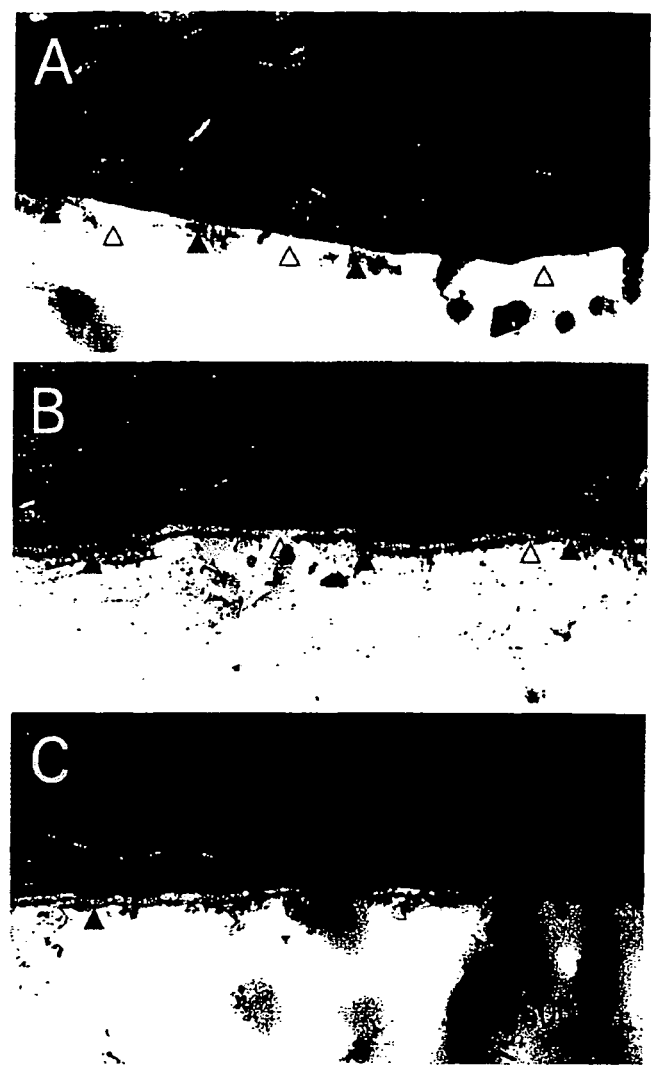
FIG. 15 is a set of transmission electron micrographs (A-C) of a respiratory epithelial tissue reconstituted on collagen fiber (fib), amorphous deposit structure (deposit—fib), and a basement membrane specimen (rBM).

Respiratory epithelial cells SPOC1 were seeded on collagen fiber (fib), amorphous deposit specimen (deposit—fib), and basement membrane structure (rBM) and cultured for a short term (3 days). FIG. 15A-C are the transmission electron micrographs respectively showing the following: FIG. 15A shows the result of culture on untreated collagen fiber (fib); FIG. 15B shows the result of culture on amorphous deposit specimen (deposit—fib); FIG. 15C shows the result of culture on the basement membrane structure (rBM). In FIG. 15, ▲ shows the places where a complete basement membrane was formed, Δ shows the places where a basement membrane was not formed. As in Example 12, in the culture on untreated collagen fiber (fib), deposits of extracellular matrices beneath the cells (▲) is very little, and the formation of anchoring filament connecting the cells and a basement membrane is consequentially little. In the culture on the basement membrane structure (rBM), an anchoring filament connecting the basement membrane lamina densa (▲) and the basal surface of the cells is well formed, it can be seen that tissue is being formed as the respiratory epithelial cells are recognizing and accepting the basement membrane structure (rBM) constructed by alveolar epithelial cells as their own basement membrane, though it is not the basement membrane formed by themselves. In the culture on amorphous deposit specimen (deposit—fib), as the deposit (▲) and the basal surface of the cells are connected by an anchoring filament as in the case of a basement membrane specimen, although tissue formation is slightly inferior compared to the case of the basement membrane structure (rBM), the formation of the basement membrane structure and anchoring filament is further progressed compared to the case of untreated collagen fiber (fib).

Example 14

Construction of a Basement membrane According to the MMP Inhibition Method

Figure 16:
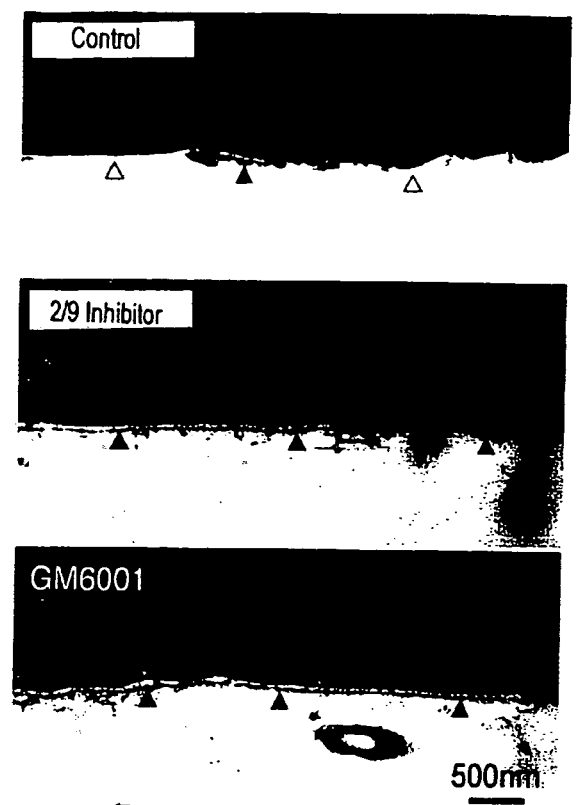
FIG. 16 is a set of transmission electron micrographs of type II alveolar epithelial tissue constituted on collagen fiber (fib) in the presence of synthetic inhibitor of matrix metalloproteinase (MMP).

Alveolar epithelial cells were cultured on collagen fiber (fib) with the only addition of 1% fetal bovine serum and synthetic inhibitor of matrix metalloproteinase (MMP) and without the addition of basement membrane components for 2 weeks. As MMP inhibitor, GM6001 (Calbiochem) and MMP-2/MMP-9 inhibitor I (Calbiochem) were used. 1.1 µM of GM6001 and 310 µM of MMP-2/MMP-9 inhibitor I (2/9 inhibitor) were added respectively. The results are shown in FIG. 16. As FIG. 16 shows, complete basement membrane structure (▲) was formed beneath the cells by the addition of synthetic MMP inhibitor. In FIG. 16, Δ shows the places where a basement membrane was not formed (Control).

Example 15

Constitution of an Artificial Tissue Exfoliated from Plastic Surface Wherein the Basement Membrane Structure is Maintained As for the adsorptive polymer by hydrophobic bonding having reactional group, alternating copolymer MMAC of methyl vinyl ether and maleic anhydride was used. MMAC was lysed in 99.5% ethanol, and MMAC solution with the concentration of 10 µg/ml was obtained. 0.5 ml of this MMAC solution was poured into the culture insert for 6-well culture plate (Becton Dickinson), it was air-dried after the excess solution was removed. This procedure was repeated for 1-3 times according to the desired extent of the temporary adhesion, then the PET membrane surface of the bottom of the culture insert was coated with MMAC. In the next place, 0.72 ml of the collagen solution containing the pulmonary fibroblasts or the solution of collagen only prepared in Example 2 was placed on the above-mentioned surface-coated PET membrane, and incubated in $CO_2$ incubator for 1 hour, or a few hours-24 hours, then pulmonary fibroblasts matrix substratum (Fgel) or high-density collagen fiber (fib) was temporarily adhered to the PET membrane surface. On this fibrous collagen substratum, type II alveolar epithelial cells (T2) were seeded and cultured for 2 weeks as in the same manner as Example 3 (T2-Fgel, or, T2-fib-Fcm or T2-fib-MG), and artificial alveolar epithelial tissue was constituted. As a result of mechanically exfoliating this artificial alveolar epithelial tissue from the PET membrane using a spatula, the artificial alveolar epithelial tissue wherein the basement membrane structure was maintained was obtained.

INDUSTRIAL APPLICABILITY

According to the method for preparing a basement membrane of the present invention 1, epithelial tissue model or endothelial tissues model having a basement membrane structure can be constituted in the moderate condition by using a polymer having specific sugar chain, and it has become possible for the basement membrane structure prepared in such method to form the epithelial tissue and endothelial tissue of other tissues. These basement membrane structure and epithelial tissue/endothelial tissue can be utilized for the purpose of medical/biological study, for the purpose of transplantation/therapy as an artificial blood vessel, an artificial lung, artificial liver, an artificial kidney, an artificial skin, an artificial cornea and the like, and for the purpose of pharmacological test and toxicity test.

According to the method for constructing a basement membrane specimen of the present invention 2, a basement membrane specimen having functions to control morphology, differentiation, proliferation, motility, function expression and the like of cells can be obtained when the certain homogenous or heterogeneous cells having an ability to form a basement membrane are seeded and cultured, and epithelial tissue model or endothelial tissues model having a basement membrane structure can be reconstituted in the moderate condition using said basement membrane specimen, and it becomes possible for the basement membrane structure prepared in such method to form epithelial tissues and endothelial tissues of other tissues. These basement membrane structure and epithelial tissue/endothelial tissue can be utilized for the purpose of medical/biological study, for the purpose of transplantation/therapy as an artificial blood vessel, an artificial lung, an artificial liver, an artificial kidney, an artificial skin, an artificial cornea and the like, and for the purpose of pharmacological test and toxicity test.

According to the process for producing reconstituted artificial tissue of the present invention 3, it is possible to produce the desired artificial tissue easily and efficiently in the short term at any time and any place when needed using the specimen such as the basement membrane and the like having functions to control morphology, differentiation, proliferation, motility, function expression and the like of cells as a common basic material for tissue constitution, and by seeding and culturing certain homogenous or heterogeneous cells to said cells which have formed said basement membrane. Further, the reconstituted artificial tissue of the present invention 3 having the cell layer and basement membrane equipped with the barrier function original to the living body such as an artificial blood vessel, an artificial lung, an artificial liver, artificial kidney, an artificial skin, an artificial cornea and the like, which are obtained by the process for producing such reconstituted artificial tissue having versatility can be used for the purpose of medical/biological study, transplantation/therapy, aid pharmacological test aid toxicity test.

According to the process for producing a basement membrane specimen or an artificial tissue which can be transplanted while maintaining the basement membrane structure of the present invention 4, the protein support structure supporting an artificial tissue or a basement membrane specimen which is adhered to plastic surface during the construction of a basement membrane or an artificial tissue, but which can be physically exfoliated from plastic surface when desired, and such exfoliated protein support structure supporting an artificial tissue or a basement membrane specimen will be able to be transplanted while maintaining the basement membrane structure, and be useful as a material for regenerative medicine such as an artificial blood vessel, an artificial lung, an artificial liver, an artificial kidney, an artificial skin, an artificial cornea and the like.

The invention will now be further described by the following numbered paragraphs:

1. A method for preparing a basement membrane wherein cells having an ability to form a basement membrane are cultured on a support structure with a sugar-chain coat which can localize a receptor having an activity to accumulate basement membrane components onto a basal surface of the cells having an ability to form a basement membrane.
2. The method for preparing a basement membrane according to paragraph 1, wherein the cells having an ability to form a basement membrane are cultured on of a support structure with both opposite surfaces coated by a sugar chain.
3. The method for preparing a basement membrane according to paragraph 1 or 2, wherein a component secreted from the cells having an ability to form a basement membrane is used as a basement membrane component.
4. The method for preparing a basement membrane according to any of paragraphs 1-3, wherein a sugar-chain coat, which can possibly adhere the cells having an ability to form a basement membrane onto a support structure through the binding between a sugar chain or a part of a sugar chain and a receptor, is used.
5. The method for preparing a basement membrane according to paragraph 4, wherein a sugar-chain coat is used, the sugar chain or a part of the sugar chain that binds to a receptor can be replaced by a basement membrane component.
6. The method for preparing a basement membrane according to any of paragraphs 1-5, wherein the support structure with a sugar-chain coat is a support structure coated with a polymer having a sugar chain.
7. The method for repairing a basement membrane according to Paragraph 6, wherein the polymer having a sugar chain is a polymer having a sugar chain with β-D-glucopyranosyl nonreducing end or 2-acetoamide-2deoxy-β-D-glucopyranosyl nonreducing end.
8. The method for preparing a basement membrane according to paragraph 7, wherein one or more types of polymers selected from PV-GlcNAc, PV-CA and PV-Lam is used as the polymer having a sugar chain.
9. The method for preparing a basement membrane according to any of paragraphs 1-8, wherein the cells having an ability to form a basement membrane are cocultured with fibroblasts or their alternatives.
10. The method for preparing a basement membrane according to any of paragraphs 1-9, wherein the cells having an ability to form a basement membrane are cultured in the presence of one or more types of basement membrane components.
11. The method for preparing a basement membrane according to any of paragraphs 1-10, wherein the cells having an ability to form a basement membrane are cultured in the presence of TGF-β (transforming growth factor).
12. The method for preparing a basement membrane according to any of paragraphs 1-11, wherein the cells having an ability to form a basement membrane are epithelial cells, endothelial cells or mesenchymal cells.
13. The method for preparing a basement membrane according to any of paragraphs 1-12, wherein the cells and/or fibroblasts having an ability to form a basement membrane are basement membrane component-hyperexpressing cells into which genes of one or more types of a basement membrane component are transfected.
14. The method for preparing a basement membrane according to any of paragraphs 1-13, wherein the support structure is a fibrous collagen.
15. A tissue model which can be obtained by the method for preparing a basement membrane according to any of paragraphs 1-14.
16. A test tissue kit including a tissue model which can be obtained by the method for preparing a basement membrane according to any of paragraphs 1-14.
17. A method for constructing a basement membrane specimen wherein cells having an ability to form a basement membrane adhered onto a support structure through a basement membrane are removed using a solvent having the ability to lyse lipid of the cells and an alkaline solution.
18. The method for constructing a basement membrane specimen according to paragraph 17, wherein the treatment to remove proteinous and nucleic residues using an alkaline solution is conducted after or at the same time as the delipidating treatment using a solvent having the ability to lyse lipid is conducted.
19. The method for constructing a basement membrane specimen according to paragraph 17 or 18, wherein the solvent having the ability to lyse lipid is a surface active agent.
20. The method for constructing a basement membrane specimen according to paragraph 19, wherein the surface active agent is Triton X-100.
21. The method for constructing a basement membrane specimen according to any of paragraphs 17-20, wherein the alkaline solution is an alkaline solution with pH 8-14.
22. The method for constructing a basement membrane specimen according to paragraph 2 L, wherein the alkaline solution is an alkaline solution with pH 9-10.
23. The method for constructing a basement membrane specimen according to any of paragraphs 17-22, wherein a protease inhibitor is further used.
24. The method for constructing a basement membrane specimen according to any of paragraphs 17-23, wherein the basement membrane is a basement membrane prepared by culturing the cells having an ability to form a basement membrane on a collagen gel wherein fibroblasts are embedded.
25. The method for constructing a basement membrane specimen according to any of paragraphs 17-24, wherein the basement membrane is a basement membrane prepared by culturing the cells having an ability to form a basement membrane on a support structure with a sugar-chain coat which can localize a receptor having an activity to accumulate a basement membrane component on the basal surface of the cells having an ability to form a basement membrane.
26. The method for constructing a basement membrane specimen according to any of paragraphs 17-25, wherein the basement membrane is a basement membrane prepared by culturing the cells having an ability to form a basement membrane in the presence of a matrix metalloproteinase.
27. The method for constructing a basement membrane specimen according to any of paragraphs 17-26, wherein the basement membrane is a basement membrane prepared by culturing a basement membrane component and/or growth factor hyperexpressing cells into which one or more types of genes and/or growth factors of a basement membrane component are introduced.
28. A basement membrane specimen which can be obtained by the method for constructing a basement membrane specimen according to any of paragraphs 17-27.
29. The basement membrane specimen according to paragraph 28, which is detached from a support structure.
30. A process for producing a reconstituted artificial tissue wherein certain cells having an ability to form a basement membrane are seeded and cultured on a basement membrane specimen or amorphously basement membrane components-deposited specimen.
31. The process for producing a reconstituted artificial tissue according to paragraph 30, wherein the cells having an ability to form a basement membrane have a different origin from that of a basement membrane specimen or amorphously basement membrane components-deposited specimen.

32. The process for producing a reconstituted artificial tissue according to paragraph 30 or 31, wherein the basement membrane specimen or the amorphously basement membrane components-deposited specimen is obtained by removing the cells having an ability to form a basement membrane which are adhered onto a support structure through a basement membrane or basement membrane components-amorphous deposits using a solvent having the ability to lyse lipid of the cells and an alkaline solution.

33. The process for producing a reconstituted artificial tissue according to paragraph 32, wherein the solvent having the ability to lyse lipid of cells is a surface active agent.

34. The process for producing a reconstituted artificial tissue according to paragraph 32 or 33, wherein the alkaline solution is an alkaline solution with pH 8-14.

35. The process for producing a reconstituted artificial tissue according to paragraph 34, wherein the alkaline solution is an alkaline solution with pH 9-10.

36. The process for producing a reconstituted artificial tissue according to any of paragraphs 32-35, wherein a protease inhibitor is further used.

37. The process for producing a reconstituted artificial tissue according to any of paragraphs 30-36, wherein the basement membrane specimen or the basement membrane components-amorphous deposits specimen is obtained from a basement membrane or a basement membrane components-amorphous deposits prepared by culturing the cells having an ability to form a basement membrane on a collagen gel wherein fibroblasts are embedded.

38. The process for producing a reconstituted artificial tissue according to any of paragraphs 30-37, wherein the basement membrane specimen or the basement membrane components-amorphous deposits specimen is obtained from a basement membrane or a basement membrane components-amorphous deposits prepared by culturing the cells having an ability to form a basement membrane on a support structure with a sugar chain-coat which can localize a receptor having an activity to accumulate a basement membrane component onto the basal surface of the cells having an ability to form a basement membrane or the surface of the basement membrane components-amorphous deposits.

39. The process for producing a reconstituted artificial tissue according to any of paragraphs 30-38, wherein the basement membrane specimen or the basement membrane components-amorphous deposits specimen is obtained from a basement membrane or a basement membrane components-amorphous deposits prepared by culturing the cells having an ability to form a basement membrane in the presence of a matrix metalloproteinase.

40. The process for producing a reconstituted artificial tissue according to any of paragraphs 30-39, wherein the basement membrane specimen or the basement membrane components-amorphous deposits specimen is obtained from a basement membrane or a basement membrane components-amorphous deposit prepared by culturing a basement membrane component and/or growth factor hyperexpressing cells into which one or more types of genes and/or growth factors of basement membrane components are transfected.

41. A reconstituted artificial tissue which can be obtained by the production process according to any of paragraphs 30-40.

42. The reconstituted artificial tissue according to paragraph 41, wherein the reconstituted artificial tissue is an artificial blood vessel, an artificial lung, an artificial liver, an artificial kidney, an artificial skin or an artificial cornea.

43. The reconstituted artificial tissue according to paragraph 41 or 42, wherein the reconstituted artificial tissue is an artificial human tissue.

44. The reconstituted artificial tissue according to any of paragraphs 41-43, which is detached from a support structure.

45. A method for testing the safety and toxicity of a test substance wherein the reconstituted artificial tissue according to any of paragraphs 41-44 is used.

46. A basement membrane specimen or an artificial tissue which is formed on a protein support structure temporarily adhered to plastic surface through an adsorptive polymer by hydrophobic bonding having a hydrophobic linear carbon skeleton and a functional group which can react with protein in a molecule.

47. The basement membrane specimen or the artificial tissue according to paragraph 46, wherein the adsorptive polymer by hydrophobic bonding is an adsorptive polymer by hydrophobic bonding shown by the following general formula [I]:

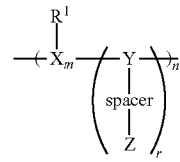

(In the formula, X denotes CH or NHCHCO, Y denotes CH or NHCR$^2$CO, R$^1$ denotes H, alkyl group of C1-C3, alkoxy group of C1-C3 or aryl group of C6-C8, R$^2$ denotes H or alkyl group of C1-C3, Z denotes a functional group (reactional group) optionally bonded to each other, spacer denotes (—CH$_2$—)p or (—NHCHR$^3$HCO—)q, R$^3$ denotes H or alkyl group of C1-C3, m denotes an integral number greater or equal to 1, n denotes an integral number between 100 and 20000, p and q independently denote 0 or integral numbers 1-8, r denotes an integral number greater or equal to 1).

48. The basement membrane specimen or the artificial tissue according to paragraph 47, wherein the adsorptive polymer by hydrophobic bonding shown by the general formula [I] is an alternating copolymer of methyl vinyl ether and maleic anhydride.

49. The basement membrane specimen or the artificial tissue according to any of paragraphs 46-48, wherein the basement membrane specimen is a basement membrane specimen constructed by removing the cells having an ability to form a basement membrane adhered onto a protein support structure through a basement membrane using a solvent having the ability to lyse lipid of the cells and an alkaline solution.

50. The basement membrane specimen or the artificial tissue according to any of paragraphs 46-49, wherein the artificial tissue is an artificial tissue prepared by culturing the cells having an ability to form a basement membrane on a protein support structure.

51. The basement membrane specimen or the artificial tissue according to any of paragraphs 46-50, wherein the artificial tissue is an artificial tissue prepared by culturing the cells having an ability to form a basement membrane on a protein support structure with a sugar-chain coat which can localize a receptor having an activity to accumulate a basement membrane component onto the basal surface of the cells having an ability to form a basement membrane.

52. The basement membrane specimen or the artificial tissue according to any of paragraphs 46-51, wherein the protein support structure is a collagen gel wherein fibroblasts are embedded.

53. The basement membrane specimen or the artificial tissue according to any of paragraphs 46-49, wherein the artificial tissue is an artificial tissue prepared by culturing the cells having an ability to form a basement membrane in the presence of a matrix metalloproteinase.

54. The basement membrane specimen or the artificial tissue according to any of paragraphs 46-53, wherein the artificial tissue is an artificial tissue prepared by culturing a basement membrane component and/or growth factor hyperexpressing cells into which one or more types of genes and/or growth factors of basement membrane components are transfected.

55. The basement membrane specimen or the artificial tissue according to any of paragraphs 46-49, wherein the artificial tissue is a reconstituted artificial tissue prepared by seeding and culturing the cells having certain ability to form a basement membrane on a basement membrane specimen.

56. The basement membrane specimen or the artificial tissue according to any of paragraphs 46-55, wherein the cells having an ability to form a basement membrane are epithelial cells or endothelial cells.

57. The basement membrane specimen or the artificial tissue according to any of paragraphs 46-56, wherein the artificial tissue is an artificial epidermal tissue, an artificial corneal epithelial tissue, an artificial alveolar epithelial tissue, an artificial respiratory epithelial tissue, an artificial renal glomerular tissue, an artificial hepatic parenchymal tissue or an artificial pulmonary arterial vascular endothelial tissue, or, an artificial blood vessel, an artificial lung, an artificial liver, an artificial kidney, an artificial skin or an artificial cornea.

58. A process for producing a basement membrane specimen or an artificial tissue which can be transplanted while maintaining the structure of a basement membrane wherein a protein support structure is temporarily adhered to plastic surface through an adsorptive polymer by hydrophobic bonding having a hydrophobic linear carbon skeleton and a functional group which can react with protein in a molecule, and abasement membrane specimen or an artificial tissue is formed thereon, and a protein support structure supporting a basement membrane specimen or an artificial tissue is physically detached from plastic surface when desired.

59. The process for producing a basement membrane specimen or an artificial tissue which can be transplanted while maintaining the structure of a basement membrane according to paragraph 58, wherein the adsorptive polymer by hydrophobic bonding is an adsorptive polymer by hydrophobic bonding shown by the following general formula [I]:

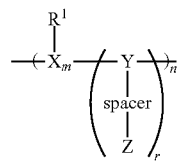

(In the formula, X denotes CH or NHCHCO, Y denotes CH or NHCR$^2$CO, R$^1$ denotes H, alkyl-group of C1-C3, alkoxy group of C1-C3 or aryl group of C6-C8, R$^2$ denotes H or alkyl group of C1-C3, Z denotes a functional group (reactional group) optionally bonded to each other, spacer denotes (—CH$_2$—)p or (—NHCHR$^3$HCO—)q, R$^3$ denotes H or alkyl group of C1-C3, m denotes an integral number greater or equal to 1, n denotes an integral number between 100 and 20000, p and q independently denote 0 or integral numbers 1-8, r denotes an integral number greater or equal to 1).

61. The process for producing a basement membrane specimen or an artificial tissue which can be transplanted while maintaining the structure of a basement membrane according to paragraph 59, wherein the adsorptive polymer by hydrophobic bonding shown by the general formula [I] is an alternating copolymer of methyl vinyl ether and maleic anhydride.

61. The process for producing a basement membrane specimen or an artificial tissue which can be transplanted while maintaining the structure of a basement membrane according to any of paragraphs 58-60, wherein the basement membrane specimen is a basement membrane specimen constructed by removing the cells having an ability to form a basement membrane adhered onto a protein support structure through basement membrane using a solvent having the ability to lyse lipid of the cells and an alkaline solution.

62. The process for producing a basement membrane specimen or an artificial tissue which can be transplanted while maintaining the structure of a basement membrane according to any of paragraphs 58-61, wherein the artificial tissue is a basement membrane prepared by culturing the cells having an ability to form a basement membrane on a protein support structure.

63. The process for producing a basement membrane specimen or an artificial tissue which can be transplanted while maintaining the structure of a basement membrane according to any of paragraphs 58-62, wherein the artificial tissue is an artificial tissue prepared by culturing the cells having an ability to form a basement membrane on a protein support structure with a sugar-chain coat which can localize a receptor having an activity to accumulate a basement membrane component onto the basal surface of the cells having an ability to form a basement membrane.

64. The process for producing a basement membrane specimen or an artificial tissue which can be transplanted while maintaining the structure of a basement membrane according to any of paragraphs 58-63, wherein the artificial tissue is a reconstituted artificial tissue prepared by seeding and culturing the cells having a certain ability to form a basement membrane on the basement membrane specimen.

65. The process for producing a basement membrane specimen or an artificial tissue which can be transplanted while maintaining the structure of a basement membrane according to any of paragraphs 58-64, wherein the cells having an ability to form a basement membrane are epithelial cells or endothelial cells.

66. The process for producing a basement membrane specimen or an artificial tissue which can be transplanted while maintaining the structure of a basement membrane according to any of paragraphs 58-65, wherein the protein support structure is a collagen gel wherein fibroblasts are embedded.

67. The process for producing the basement membrane specimen or the artificial tissue which can be transplanted while maintaining the structure of a basement membrane according to any of paragraphs 58-66, wherein the artificial tissue is an artificial epidermal tissue, an artificial corneal epithelial tissue, an artificial alveolar epithelial tissue, an artificial respiratory epithelial tissue, an artificial renal glomerular tissue, an artificial hepatic parenchymal tissue or an artificial pulmonary arterial vascular endothelial tissue, or, an artificial blood vessel, an artificial lung, an artificial liver, an artificial kidney, an artificial skin or an artificial cornea.

The invention claimed is:

1. A process for producing a reconstituted artificial tissue wherein the process comprises the following steps:
   (a) seeding and culturing homogenous or heterogeneous cells having an ability to form a basement membrane to provide either (i) a basement membrane specimen having a function to control morphology, differentiation, proliferation, and motility of cells, or (ii) a basement membrane components-amorphous deposits specimen which is an incomplete basement membrane comprised of amorphous structure irregularly containing basement membrane components;

(b) seeding and culturing cells having an ability to form a basement membrane on the basement membrane specimen or the basement membrane components-amorphous deposits specimen; and (c) reconstituting an artificial tissue on the basement membrane specimen or the basement membrane components-amorphous deposits specimen;

wherein the basement membrane specimen or the basement membrane components-amorphous deposits specimen in step (a) is obtained from a basement membrane or a basement membrane components-amorphous deposits prepared by culturing the cells having an ability to form a basement membrane on a support structure with a sugar chain-coat that can localize a receptor;

wherein the receptor has an activity to accumulate a basement membrane component onto (i) the basal surface of the cells having an ability to form a basement membrane, or (ii) the surface of the basement membrane components-amorphous deposits; and wherein the sugar-chain coat has a B-D-glucopyranosyl non-reducing end or a 2-acetoamide-2-deoxy-B-D-glucopyranosyl non-reducing end.

2. The process for producing a reconstituted artificial tissue according to claim 1, wherein the cells having an ability to form a basement membrane in step (b) have a different origin from that of the basement membrane specimen or amorphously basement membrane components-amorphous deposits specimen.

3. The process for producing a reconstituted artificial tissue according to claim 1, wherein step (a) further comprises the following steps:

(i) subjecting the cells adhered onto a support structure through a basement membrane to a delipidating treatment using a solvent having the ability to lyse lipid of the cells;

(ii) conducting a treatment to remove proteinous and nucleic residues using an alkaline solution after or at the same time as the delipidating treatment; and (iii) when the cells are detached, seeding and culturing homogenous or heterogeneous cells having an ability to form a basement membrane, and exposing a basement membrane having a function to control morphology, differentiation, proliferation, and motility of cells.

4. The process for producing a reconstituted artificial tissue according to claim 3, wherein the solvent having the ability to lyse lipid of cells in step (i) is a surface active agent.

5. The process for producing a reconstituted artificial tissue according to claim 3, wherein the alkaline solution in step (ii) is an alkaline solution with pH 8-14.

6. The process for producing a reconstituted artificial tissue according to claim 5, wherein the alkaline solution in step (ii) is an alkaline solution with pH 9-10.

7. The process for producing a reconstituted artificial tissue according to claim 3, wherein a protease inhibitor is used in step (i) and step (ii) to suppress degradation of the basement membrane.

8. The process for producing a reconstituted artificial tissue according to claim 1, wherein said support structure is a collagen gel into which fibroblasts are embedded.

9. The process for producing a reconstituted artificial tissue according to claim 1, wherein the basement membrane specimen or the basement membrane components-amorphous deposits specimen in step (a) is obtained from a basement membrane or a basement membrane components-amorphous deposits prepared by culturing the cells having an ability to form a basement membrane in the presence of a matrix metalloproteinase inhibitor.

10. The process for producing a reconstituted artificial tissue according to claim 1, wherein the basement membrane specimen or the basement membrane components-amorphous deposits specimen in step (a) is obtained from a basement membrane or a basement membrane components-amorphous deposit prepared by culturing a basement membrane component and/or growth factor hyperexpressing cells into which one or more types of genes and/or growth factors of basement membrane components are transfected.

* * * * *

UNITED STATES PATENT AND TRADEMARK OFFICE
CERTIFICATE OF CORRECTION

PATENT NO. : 8,765,473 B2
APPLICATION NO. : 11/599953
DATED : July 1, 2014
INVENTOR(S) : Katsumi Mochitate et al.

It is certified that error appears in the above-identified patent and that said Letters Patent is hereby corrected as shown below:

IN THE CLAIMS:

In claim 1, column 41, line 26:

"B-D-glucopyranosyl" should read --β-D-glucopyranosyl--

In claim 1, column 41, lines 27-28:

"2-acetoamide-2-deoxy-B-D-glucopyranosyl" should read --2-acetoamide-2-deoxy-β-D-glucopyranosyl--

In claim 2, column 41, lines 32-33:

Please remove the term "amorphously"

Signed and Sealed this
Sixth Day of January, 2015

Michelle K. Lee
*Deputy Director of the United States Patent and Trademark Office*